United States Patent
D'Alessandro et al.

(10) Patent No.: US 11,564,636 B1
(45) Date of Patent: **\*Jan. 31, 2023**

(54) SYSTEM AND METHOD FOR PHYSIOLOGICAL HEALTH SIMULATION

(71) Applicant: PricewaterhouseCoopers LLP, New York, NY (US)

(72) Inventors: Paul M. D'Alessandro, Lake Forest, IL (US); Mark Paich, Littleton, CO (US); Samuel Pierce Burns, Philadelphia, PA (US); Joydeep Sarkar, Arlington, VA (US); Gaurav Dwivedi, Atlanta, GA (US); Colleen Chelini, Mill Valley, CA (US)

(73) Assignee: PricewaterhouseCoopers LLP, New York, NY (US)

( * ) Notice: Subject to any disclaimer, the term of this patent is extended or adjusted under 35 U.S.C. 154(b) by 746 days.

This patent is subject to a terminal disclaimer.

(21) Appl. No.: 16/529,339

(22) Filed: Aug. 1, 2019

Related U.S. Application Data

(62) Division of application No. 15/096,022, filed on Apr. 11, 2016, now Pat. No. 10,398,389.

(51) Int. Cl.
*A61B 5/00* (2006.01)
*A61B 5/145* (2006.01)

(52) U.S. Cl.
CPC ........ *A61B 5/7275* (2013.01); *A61B 5/14532* (2013.01); *A61B 5/14546* (2013.01); *A61B 5/425* (2013.01)

(58) Field of Classification Search
CPC ....... A61B 5/00; A61B 5/145; A61B 5/14532; A61B 5/14546; A61B 5/425; A61B 5/7275; A61K 31/138; A61K 31/7004; A61K 31/741; G16H 50/30

See application file for complete search history.

(56) References Cited

U.S. PATENT DOCUMENTS

| | | | |
|---|---|---|---|
| 7,024,369 | B1 | 4/2006 | Brown et al. |
| 7,967,731 | B2 | 6/2011 | Kil |
| 8,423,113 | B2 | 4/2013 | Shariati et al. |
| 8,521,556 | B2 | 8/2013 | Chbat et al. |
| 8,612,454 | B2 | 12/2013 | Charles et al. |
| 8,775,200 | B1 | 7/2014 | Dunn et al. |
| 2004/0254736 | A1 | 12/2004 | Michelson et al. |
| 2008/0183060 | A1 | 7/2008 | Steil et al. |
| 2010/0168539 | A1 * | 7/2010 | Palerm .................. G16H 50/20 600/365 |
| 2011/0160555 | A1 | 6/2011 | Reifman et al. |

(Continued)

FOREIGN PATENT DOCUMENTS

| | | |
|---|---|---|
| CN | 103649987 A | 3/2014 |
| CN | 106687119 A1 * | 7/2015 |

(Continued)

OTHER PUBLICATIONS

NPL Search (May 25, 2022).*

(Continued)

*Primary Examiner* — Van T Trieu
(74) *Attorney, Agent, or Firm* — Morrison & Foerster LLP

(57) ABSTRACT

Systems and methods for health and body simulations in order to predict numerous physiological parameters in a subject or a population of subjects based on the input of limited physiological data.

28 Claims, 20 Drawing Sheets

(56) References Cited

U.S. PATENT DOCUMENTS

| | | | |
|---|---|---|---|
| 2013/0297222 A1* | 11/2013 | Callicoat | G16B 99/00 702/19 |
| 2013/0325505 A1 | 12/2013 | Vengco | |
| 2014/0172461 A1 | 6/2014 | Rogers | |
| 2014/0278527 A1 | 9/2014 | Brush | |
| 2016/0180040 A1 | 6/2016 | Ryan et al. | |
| 2017/0311897 A1 | 11/2017 | Faccioli et al. | |

FOREIGN PATENT DOCUMENTS

| | | | |
|---|---|---|---|
| CN | 101794138 A1 * | 1/2016 | |
| WO | 2015/008567 A1 | 1/2015 | |

OTHER PUBLICATIONS

Cheng, L. et al. (Jun. 2010). "An integrative model of respiratory and cardiovascular control in sleep-disordered breathing," Respiratory Physiology & Neurobiology, 174(1): 4-28.

D'Alesandro, et al., U.S. Office Action dated Nov. 19, 2018, directed to U.S. Appl. No. 15/096,022; 11 pages.

De Gaetano, A. et al. (Sep. 2008) "Mathematical models of diabetes progression," Am J Physiol Endocrinol Metab 295: E1462-E1479.

Graham, E. J.. (Aug. 2012). "Mathematical Models of Mechanisms Underlying Long-Term Type 2 Diabetes Progression," The University of Utah, Department of Mathematics, 106 pages.

Hall, K. D. (Nov. 2009). "Predicting metabolic adaptation, body weight change, and energy intake in humans," Am J Physiol Endocrinol Metab 298: E449-E466.

Huang, C. et al. (Aug. 2014). "Using Hemoglobin A1C as a Predicting Model for Time Interval from Pre-Diabetes Progressing to Diabetes," PLoS One 9(8): e104263:1-7.

Lerner, N. et al. (2014). "Predicting type 2 diabetes mellitus using haemoglobin A1c: a community-based historic cohort study," European Journal of General Practice 20:100-106.

D'Alessandro et al., U.S. Office Action dated Jun. 3, 2022, directed to U.S. Appl. No. 16/529,350; 10 pages.

D'Alessandro et al., U.S. Office Action dated Jun. 3, 2022, directed to U.S. Appl. No. 16/529,469; 8 pages.

D'Alessandro et al., U.S. Office Action dated May 31, 2022, directed to U.S. Appl. No. 16/529,330; 8 pages.

Search results in U.S. Office Action dated Jun. 3, 2022, directed to U.S. Appl. No. 16/529,350; 2 pages.

Search results in U.S. Office Action dated May 31, 2022, directed to U.S. Appl. No. 16/529,330; 2 pages.

* cited by examiner

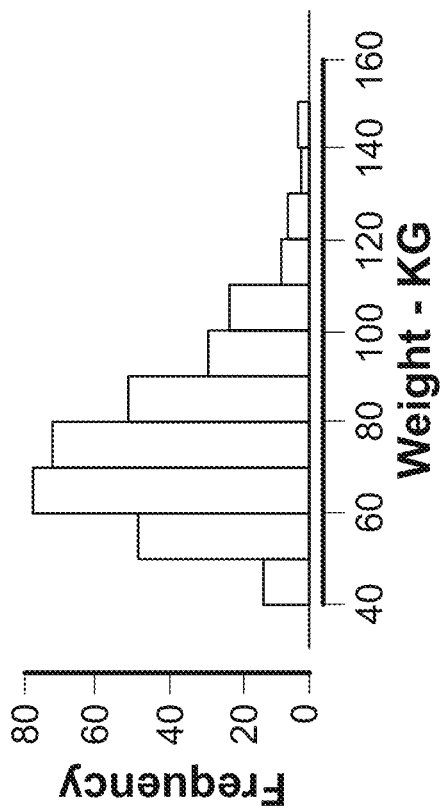
FIG. 12A 1999 - Weight
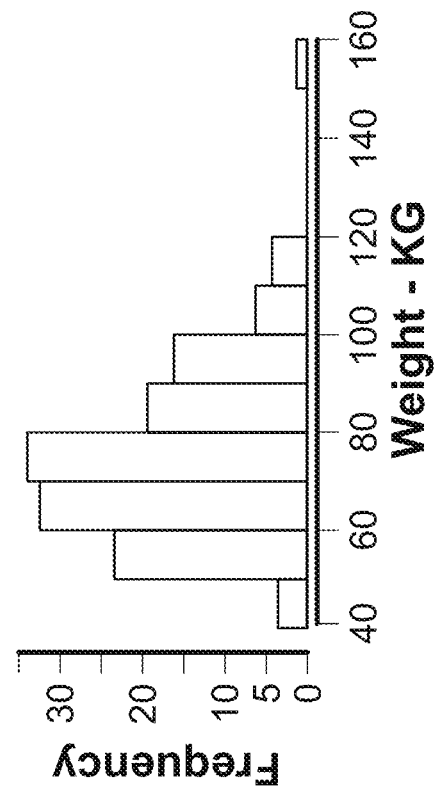
FIG. 12B 2001 - Weight
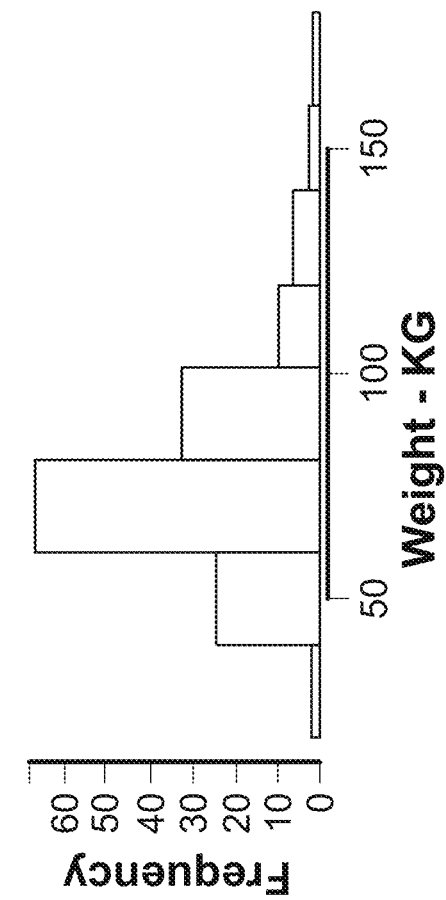
FIG. 12C 2003 - Weight
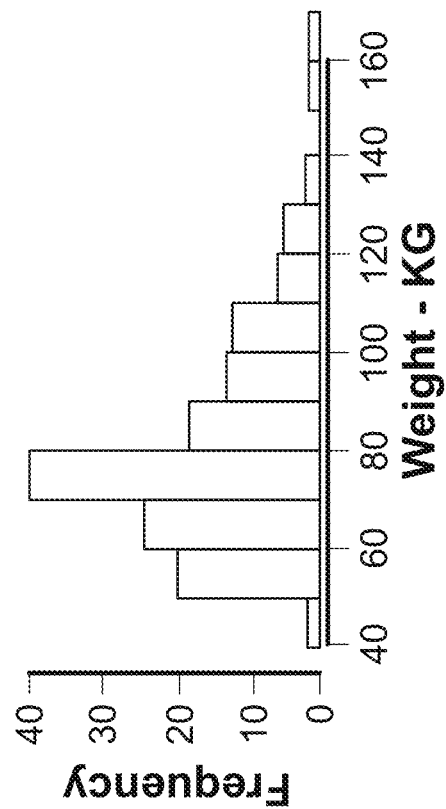
FIG. 12D 2005 - Weight

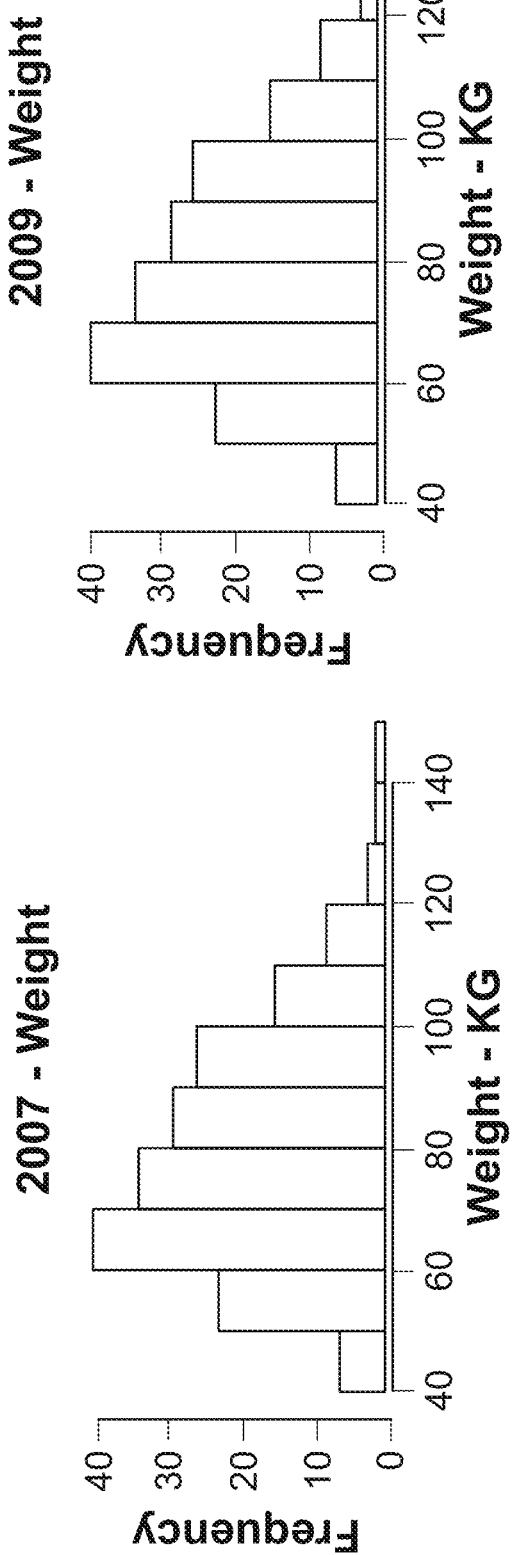
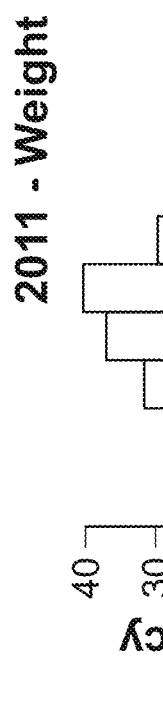
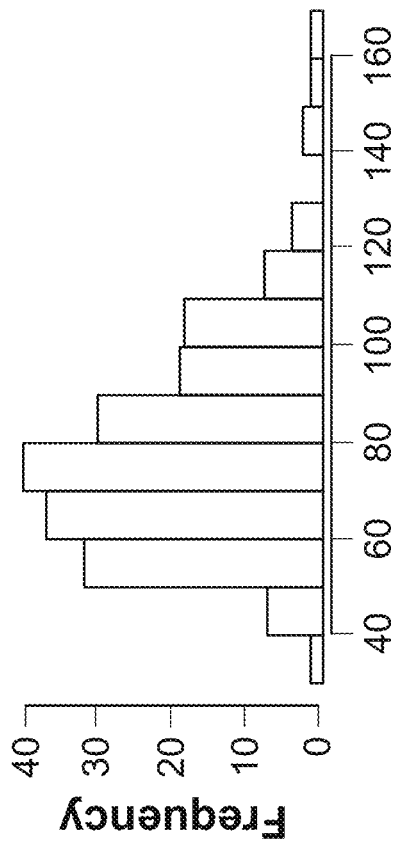
FIG. 13A
FIG. 13B
FIG. 13C

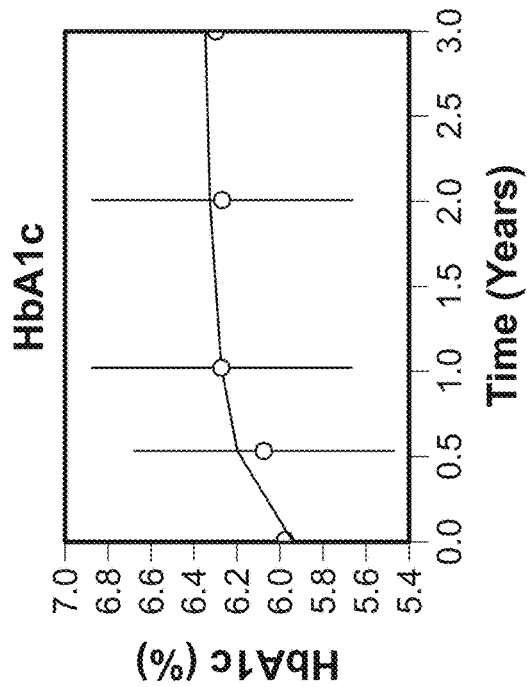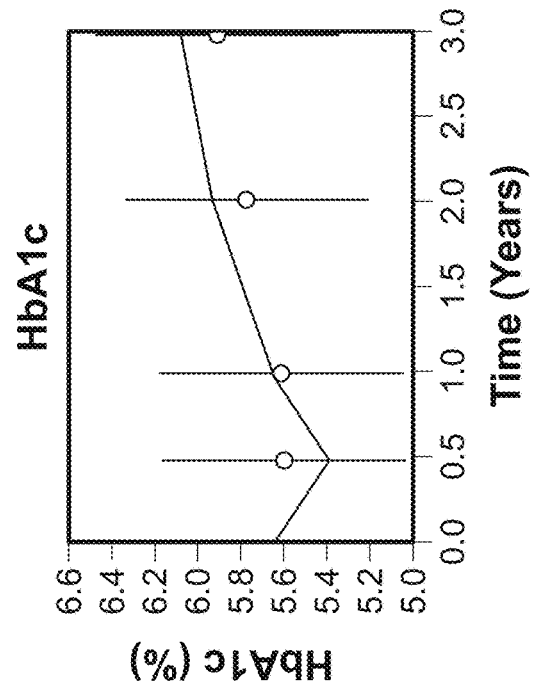
FIG. 15A
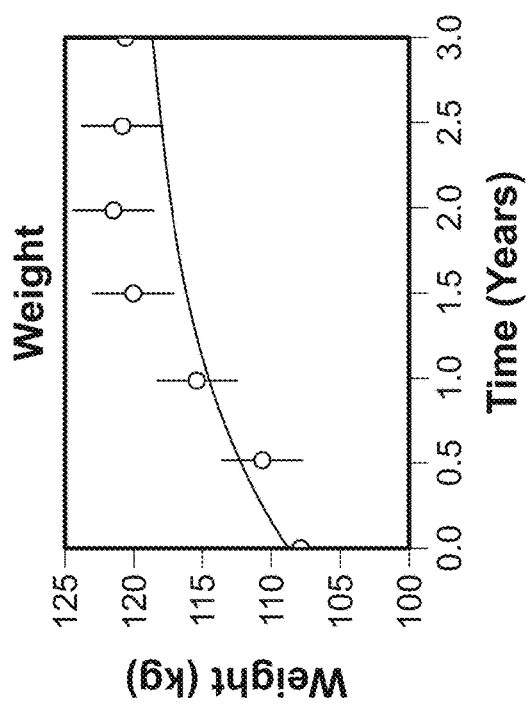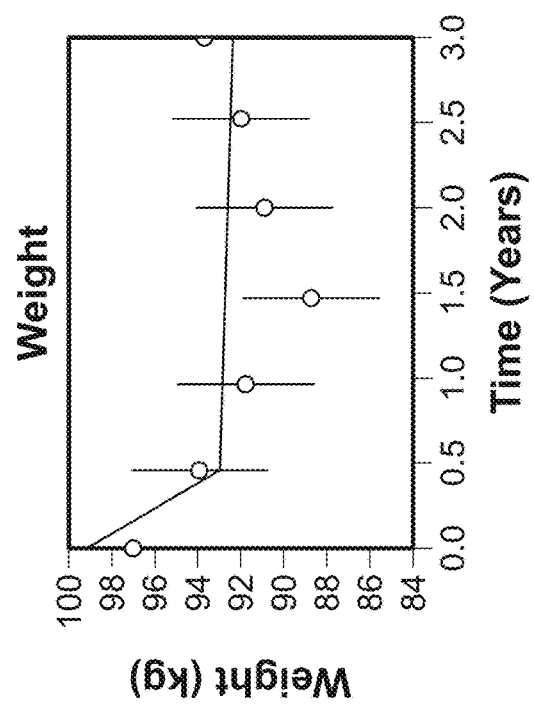
FIG. 15B

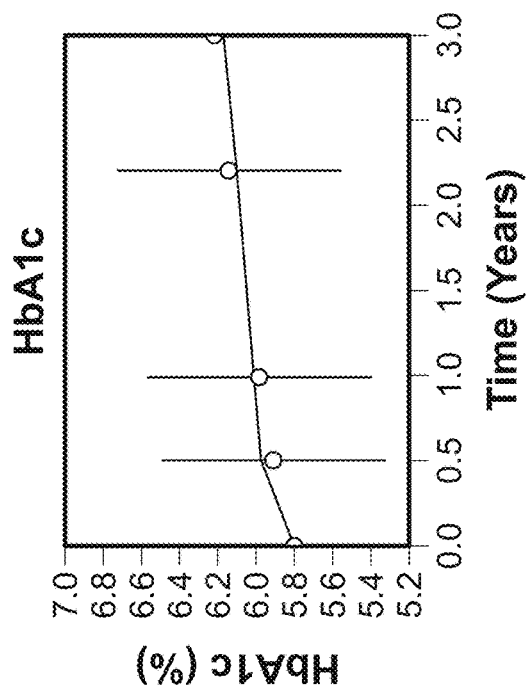
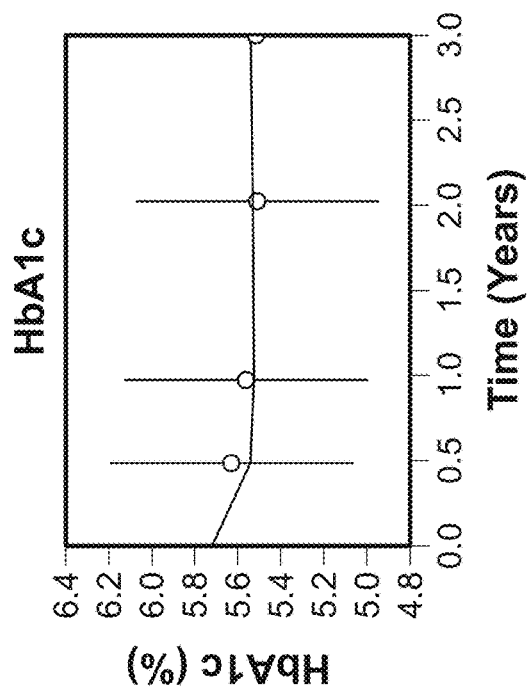
FIG. 15C
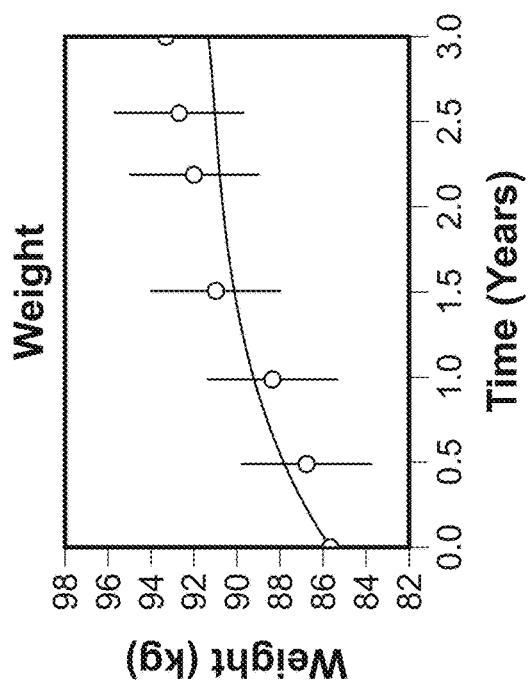
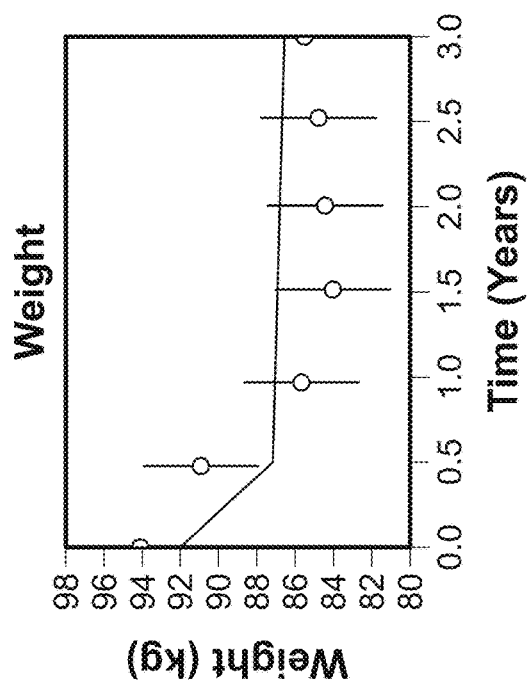
FIG. 15D

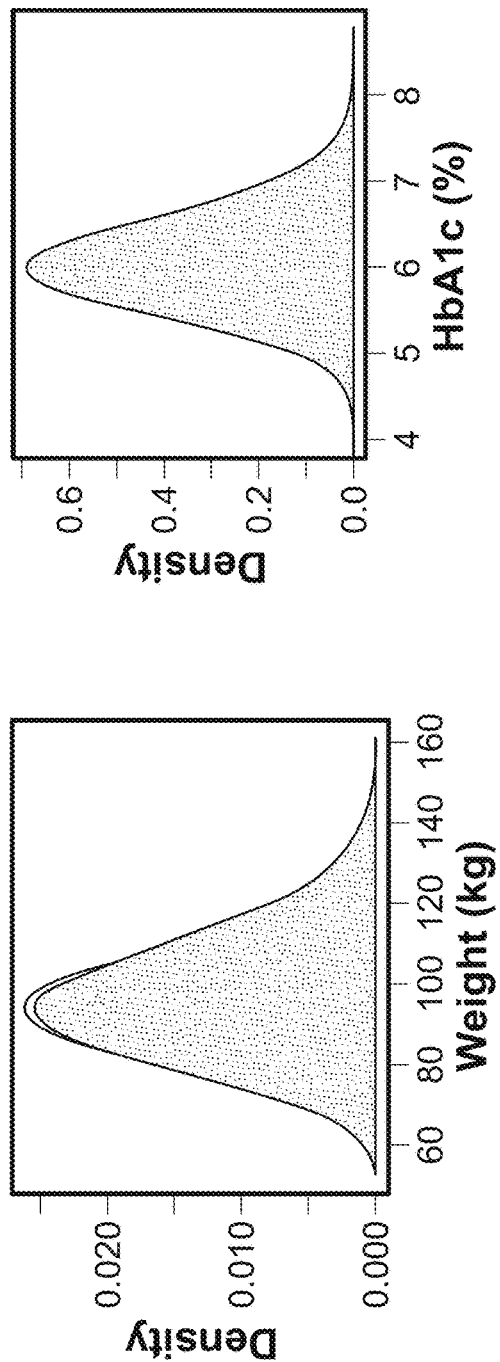
FIG. 16A
FIG. 16B
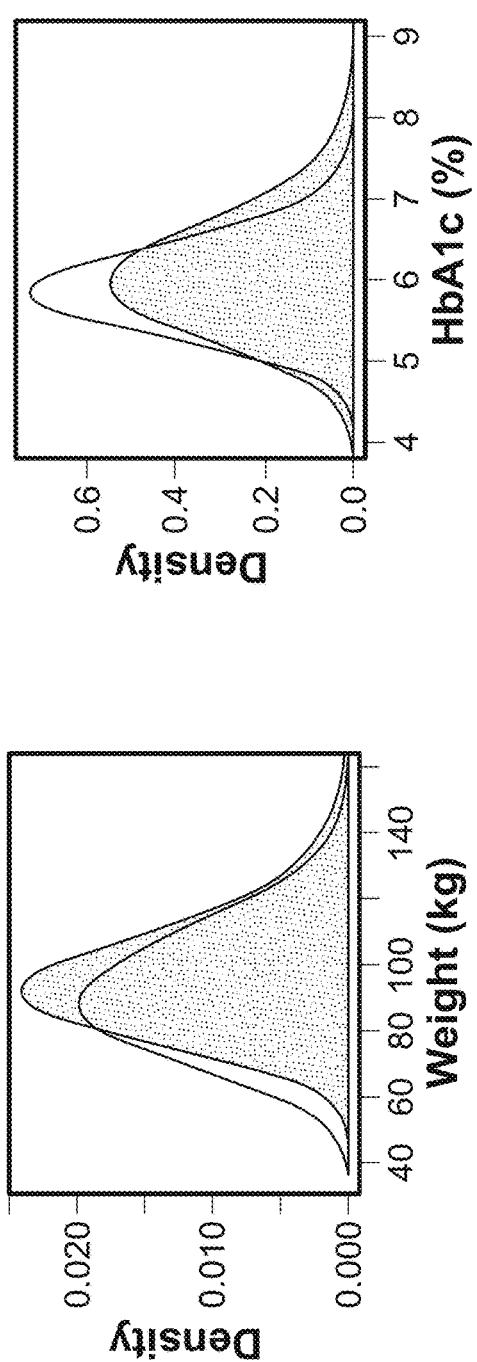
FIG. 16C
FIG. 16D

SYSTEM AND METHOD FOR PHYSIOLOGICAL HEALTH SIMULATION

CROSS REFERENCE TO RELATED APPLICATIONS

This application is a divisional application of U.S. patent application Ser. No. 15/096,022, filed Apr. 11, 2016, now U.S. Pat. No. 10,398,389, the disclosure of which is herein incorporated by reference in its entirety.

FIELD OF THE INVENTION

This invention relates to methods and systems for modeling and predicting the progression of human disease including, for example, diabetes.

BACKGROUND

We live in a new era of data availability, understanding of human physiology, and computing power with lives being remotely monitored due to sensor availability and the expansion of electronic medical records (EMRs). We can use these new advances to change how we approach health using simulation modeling much like weather modeling in 1960s and nuclear weapons simulations in 1980s. If we can use science and physiology to understand the impact of health interventions prior to implementation, we can calculate the economic value of an intervention, to build a business case prior to an implementation, and identify the right behaviors for change.

Currently, systems used to study human physiology model singular physiological processes in the body without taking into account the impact of rich interconnections and feedbacks between the many processes in the whole body. These feedbacks and interconnections between physiological processes combined with our improved understanding of the systems are critical for understanding the observed health state of an individual. Interventions modeled without considering whole body physiology are therefore insufficient to simulate health interventions at the level of an individual and cannot connect overall health outcomes to interventions.

In view of the foregoing, a need exists for an improved system and method for physiological health simulation in an effort to overcome the aforementioned obstacles and deficiencies of conventional systems.

SUMMARY OF THE INVENTION

One aspect includes a method for predicting a time to diabetes onset in a subject that includes (a) determining for the subject a subject parameter set values comprising height, weight, age, gender, and serum HbA1c concentration at a first time; (b) calculating initial parameter set values, comprising basal metabolic rate, excess caloric intake, EC50 (FFA), and beta cell apoptosis rate, from the subject parameter set by (i) setting an age estimate to an age younger than the age determined in step (a), setting a weight estimate to a weight that is different from the weight determined in step (a), and setting a serum HbA1c estimate to a value different from the serum HbA1c concentration determined in step (a), (ii) providing an initial estimate for each value in the initial parameter set values at the age estimate, (iii) iterative calculating initial parameter set values, weight estimate, and serum HbA1c estimate, in a time-dependent manner in which the age estimate is increased by a first time step in each iteration from the age estimate set is step (b)(i) to the age, such that the weight estimate is substantially equal to the weight and the serum HbA1c estimate is substantially equal to the serum HbA1c concentration when the age estimate is substantially equal to the age, (c) iteratively calculating at a future time, in a time-dependent manner in which the time is increased by a second time step, a projected serum HbA1c concentration using the initial parameter set calculated in step (b)(iii) and the subject parameter set values, until the projected serum HbA1c concentration at the second time is calculated to be greater than or equal to 6.5%, (d) identifying the future time iteratively calculated in step (c) as the time to diabetes onset, and (e) displaying the future time identified in step (d) as the predicted time for diabetes onset.

Another aspect includes a method for predicting a time to diabetes onset in a subject, the method comprising (a) determining for the subject a subject parameter set values comprising height, weight, age, gender, fasting blood glucose concentration, and serum HbA1c concentration at a first time; (b) calculating initial parameter set values, comprising basal metabolic rate, excess caloric intake, EC50 (FFA), and beta cell apoptosis rate, from the subject parameter set by (i) setting an age estimate to an age younger than the age determined in step (a), setting a weight estimate to a weight that is different from the weight determined in step (a), setting a fasting blood glucose concentration estimate to a value different from the fasting blood glucose concentration determined in step (a), and setting a serum HbA1c estimate to a value different from the serum HbA1c concentration determined in step (a) (ii) providing an initial estimate for each value in the initial parameter set values at the age estimate, (iii) iterative calculating initial parameter set values, weight estimate, fasting blood glucose concentration estimate, and serum HbA1c estimate, in a time-dependent manner in which the age estimate is increased by a first time step in each iteration from the age estimate set is step (b)(i) to the age, such that the weight estimate is substantially equal to the weight, the fasting blood glucose concentration estimate is substantially equal to the fasting blood glucose concentration, and the serum HbA1c estimate is substantially equal to the serum HbA1c concentration when the age estimate is substantially equal to the age, (c) iteratively calculating at a future time, in a time-dependent manner in which the time is increased by a second time step, a projected fasting blood glucose concentration using the initial parameter set calculated in step (b)(iii) and the subject parameter set values, until the projected fasting blood glucose concentration at the second time is calculated to be greater than 125 mg/dL, (d) identifying the future time iteratively calculated in step (c) as the time to diabetes onset, and (e) displaying the future time identified in step (d) as the predicted time for diabetes onset.

In some embodiments, the fasting blood glucose concentration estimate set in step (b)(i) is less than 100 mg/dL.

Another aspect includes a method for predicting a future blood glucose concentration in a subject, the method comprising: (a) determining for the subject a subject parameter set values comprising height, weight, age, gender, fasting blood glucose concentration, and serum HbA1c concentration at a first time; (b) calculating initial parameter set values, comprising basal metabolic rate, excess caloric intake, EC50(FFA), and beta cell apoptosis rate, from the subject parameter set by (i) setting an age estimate to an age younger than the age determined in step (a), setting a weight estimate to a weight that is different from the weight determined in step (a), setting a fasting blood glucose concentration estimate to a value different from the fasting blood glucose concentration determined in step (a), and setting a serum HbA1c estimate to a value different from the serum HbA1c concentration determined in step (a) (ii) providing an initial estimate for each value in the initial parameter set values at the age estimate, (iii) iterative calculating initial parameter set values, weight estimate, fasting blood glucose concentration estimate, and serum HbA1c estimate, in a time-dependent manner in which the age estimate is increased by a first time step in each iteration from the age estimate set is step (b)(i) to the age, such that the weight estimate is substantially equal to the weight, the fasting blood glucose concentration estimate is substantially equal to the fasting blood glucose concentration, and the serum HbA1c estimate is substantially equal to the serum HbA1c concentration when the age estimate is substantially equal to the age, (c) iteratively calculating at a future time, in a time-dependent manner in which the time is increased by a second time step, a projected fasting blood glucose concentration using the initial parameter set calculated in step (b)(iii) and the subject parameter set values, and (d) displaying the projected fasting blood glucose concentration iteratively calculated in step (c) at a plurality of future times.

In some embodiments, the fasting blood glucose concentration estimate set in step (b)(i) is less than 100 mg/dL.

Another aspect includes a method for predicting a future weight of a subject, the method comprising: (a) determining for the subject a subject parameter set values comprising height, weight, age, gender, and serum HbA1c concentration at a first time; (b) calculating initial parameter set values, comprising basal metabolic rate, excess caloric intake, EC50 (FFA), and beta cell apoptosis rate, from the subject parameter set by (i) setting an age estimate to an age younger than the age determined in step (a), setting a weight estimate to a weight that is different from the weight determined in step (a), and setting a serum HbA1c estimate to a value different from the serum HbA1c concentration determined in step (a), (ii) providing an initial estimate for each value in the initial parameter set values at the age estimate, (iii) iterative calculating initial parameter set values, weight estimate, and serum HbA1c estimate, in a time-dependent manner in which the age estimate is increased by a first time step in each iteration from the age estimate set is step (b)(i) to the age, such that the weight estimate is substantially equal to the weight, and the serum HbA1c estimate is substantially equal to the serum HbA1c concentration when the age estimate is substantially equal to the age, (c) iteratively calculating at a future time, in a time-dependent manner in which the time is increased by a second time step, a projected weight using the initial parameter set calculated in step (b)(iii) and the subject parameter set values, and (d) displaying the projected weight iteratively calculated in step (c) at a plurality of future times.

Another aspect includes a method for predicting a future mass of pancreatic beta cells in a subject, the method comprising: (a) determining for the subject a subject parameter set values comprising height, weight, age, gender, serum insulin concentration, serum glucose concentration, and serum HbA1c concentration at a first time; (b) calculating initial parameter set values, comprising basal metabolic rate, excess caloric intake, EC50(FFA), and beta cell apoptosis rate, from the subject parameter set by (i) setting an age estimate to an age younger than the age determined in step (a), setting a weight estimate to a weight that is different from the weight determined in step (a), setting a serum insulin concentration estimate to a serum insulin concentration that is different from the serum insulin concentration determined in step (a), setting a serum glucose concentration estimate to a serum glucose concentration that is different from the serum glucose concentration determined in step (a), and setting a serum HbA1c estimate to a value different from the serum HbA1c concentration determined in step (a), (ii) providing an initial estimate for each value in the initial parameter set values at the age estimate, (iii) iterative calculating initial parameter set values, weight estimate, serum insulin concentration estimate, serum glucose concentration estimate, and serum HbA1c estimate, in a time-dependent manner in which the age estimate is increased by a first time step in each iteration from the age estimate set is step (b)(i) to the age, such that the weight estimate is substantially equal to the weight, the serum insulin concentration estimate is substantially equal to the serum insulin concentration, the serum glucose concentration estimate is substantially equal to the serum glucose concentration, and the serum HbA1c estimate is substantially equal to the serum HbA1c concentration when the age estimate is substantially equal to the age, (c) iteratively calculating at a future time, in a time-dependent manner in which the time is increased by a second time step, a projected mass of pancreatic beta cells using the initial parameter set calculated in step (b)(iii) and the subject parameter set values, and (d) displaying the projected mass of pancreatic beta cells iteratively calculated in step (c) at a plurality of future times.

In any of the foregoing aspects of the invention, the age estimate set in step (b)(i) is at least one year less than the age.

In any of the foregoing aspects of the invention, the weight estimate set in step (b)(i) is less than the weight.

In any of the foregoing aspects of the invention, the serum HbA1c estimate set in step (b)(i) is less than 3%.

In any of the foregoing aspects of the invention, the first time step is 5-365 days.

In any of the foregoing aspects of the invention, the first time step is constant for all iterations.

In any of the foregoing aspects of the invention, the second time step is 5-365 days.

In any of the foregoing aspects of the invention, the second time step is constant for all iterations.

By "excess caloric intake" is meant the caloric intake of a subject which exceeds the amount of calories consumed over the same time period as calculated using the actual or estimated basal metabolic rate (BMR). For convenience, the BMR and excess caloric intake is expressed as kcal/day but these measures may be expressed as any suitable measure of nutritional energy equivalent (e.g., kilojoules) and/or over any suitable time period (e.g., hours, days, weeks, years, etc.).

By "EC50(FFA)" is meant the half maximal free fatty acid (FFA) concentration in muscle that induces insulin resistance in a subject.

By "beta cell apoptosis rate" is meant the proportion of existing pancreatic beta cells in a subject that undergo apoptosis, as a function of time. For convenience, this is expressed as a proportion (i.e., range of 0-1) and is expressed on a daily basis.

BRIEF DESCRIPTION OF THE DRAWINGS

FIGS. 12A-D and 13A-C show bar graphs of the body weight for women initially between the ages of 50-55 starting in 1999 and then in 2001, 2003, 2005, 2007, 2009 and 2011 respectively.

FIGS. 15A-D illustrate four sample subjects to demonstrate the method of simulation disclosed in FIGS. 1-4.

FIGS. 16A-D illustrate the comparison of experimental data and model output representing a distribution of weight and HbA1C as a baseline for the placebo population (A-B) and predictions for the lifestyle-modification arm (C-D).

Figure 1:
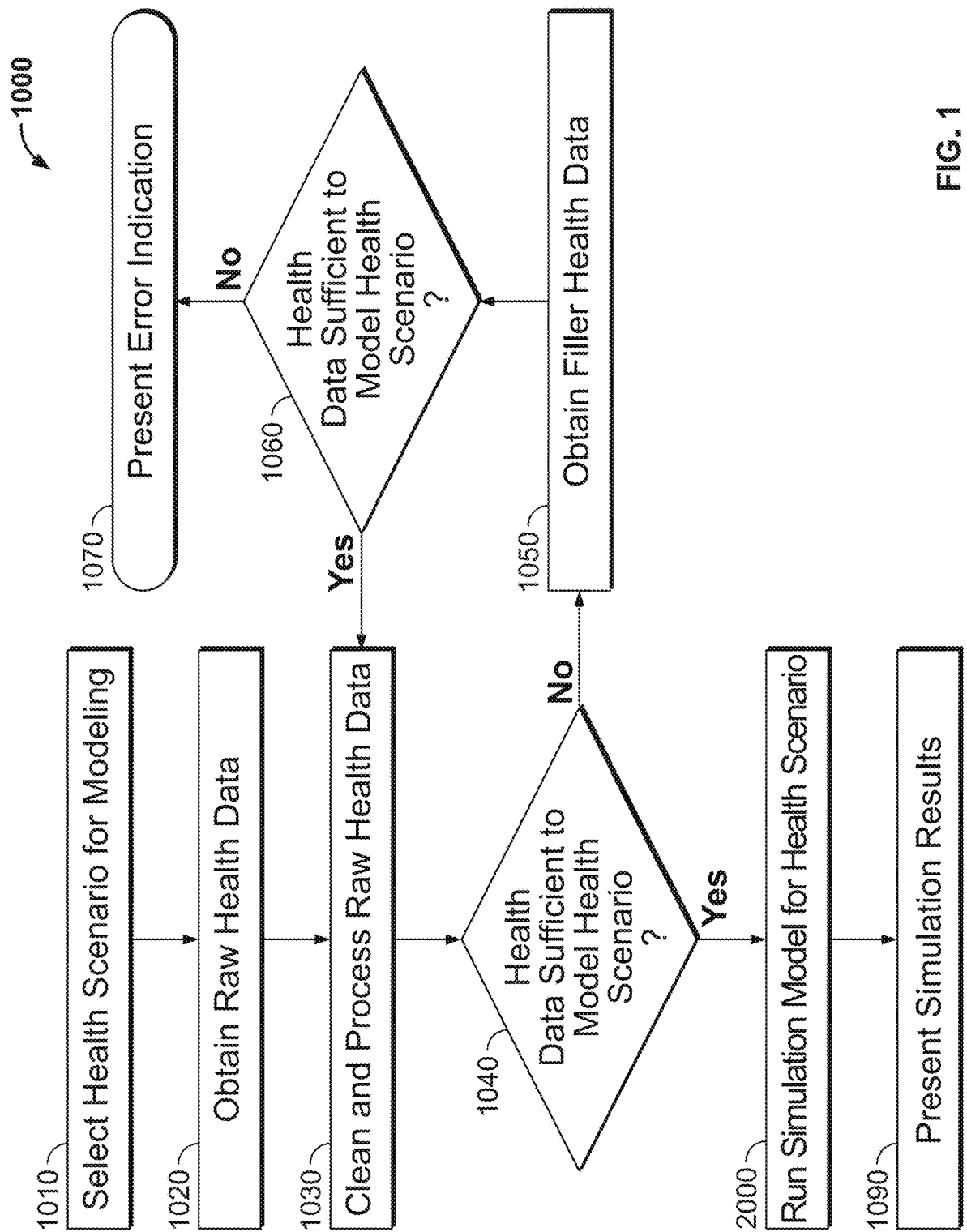
FIG. 1 is an exemplary flow chart illustrating an embodiment of a method of simulating a biological process.

It should be noted that the figures are not drawn to scale and that elements of similar structures or functions are generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION OF THE PREFERRED EMBODIMENTS

Currently available models of human physiological systems are deficient because they model body systems in isolation without accounting for the rich connections between systems. Thus, there is a need for an improved physiological health and body simulation system that can provide a platform for a wide range of applications, such as selection of cost effective health interventions, guiding users through a health intervention, and understanding the impact of lifestyle, drugs, or medical devices. This result can be achieved, according to the health and body simulation systems disclosed herein. The health and body simulations may be provided as a stand-alone module or may be integrated into other health and wellness products including, for example, dietary and fitness tracking programs and applications for research and development in drug development.

In various embodiments, and as described in more detail herein, the health and body simulation system can be configured to model human physiology to predict future health states, effects of various health intervention strategies and optimize these interventions at an individual patient level in a medical setting with the end goal of enabling health providers to choose patient-specific combinations of pharmaceutical and/or lifestyle interventions; and/or keeping patients engaged by making them aware of long term consequences of lifestyle choices and enabling them to make informed decisions. Additionally, in some embodiments, the health and body simulation system can be configured to integrate patient-specific data from multiple sources into a single platform that can consume this data and provide useful insights and predictions about body health on an individual, group or demographic level.

The patient data can come from a variety of sources. For example, patient specific electronic medical records (EMRs) can be available to the provider, and these records can contain physiological measurements such as blood pressure, blood glucose, previous medication history, and the like. Patient specific data can also be available from wearable user devices such as fitness bands, pedometers, smart watches, and the like. Some user devices, and the health and body simulation system generally, also may allow for the manual entry of data including, for example, lifestyle or user information such as type, intensity and duration of exercise, sleep patterns, gender, height, weight, and the like.

In various embodiments, the present system can be configured to allow payers, providers, pharmaceutical and life science companies, employers, government, and wellness organizations, and the like, to leverage the predictive power of the simulation module to identify future high-risk patients. Identification of future high-risk patients can allow for early interventions to prevent future over-utilization of health resources. Additionally, in various embodiments, organizations can quantify effects of intervention programs on populations as described in more detail herein. By providing a system dynamics approach to modeling, the body simulation module can provide mechanism-based quantitative analysis to drive and inform complex business decisions on health and wellness expenditures.

In further embodiments, as described herein, the body simulation module can be used to simulate clinical trials, which are expensive with long lead-times and associated with high risks of failure. In various embodiments, the body simulation module can provide for an initial assessment of new pharmaceutical products in a virtual, non-invasive in silico environment. Pharmaceutical and life science companies, academic institutions and the like can thereby evaluate product efficacy on a large simulated population prior to a full clinical trial allowing the organizations to manage their pipeline and investment dollars more effectively. Such a strategy of using simulation results to supplement experimental and clinical evidence is currently promoted by the Food and Drug Administration (FDA). Additionally, companies can use simulated clinical trials to identify adverse side effects arising from complex systemic interactions. In an environment of increasing regulation of pharmaceutical products, this extra layer of protection can identify and mitigate potential risks early in the drug development process.

In some embodiments, consumer-facing organizations can use the body simulation module to design and develop applications to provide personal behavior nudges and guide individuals to better levels of personalized health. The body simulation module therefore can provide quantitative, scientific backing for external applications to recommend behavioral changes and inform individuals to make educated health decisions.

In further embodiments, the body simulation module can be configured to allow clinicians to proactively model the relationships between body subcomponents to understand treatment effects in multiple sub-systems of the body. Providers can use the body simulation module to simulate a variety of intervention options to understand the potential impact of each, which can then inform their clinical decisions. By running optimization simulations for an individual, the right specifications of interventions can be identified.

Implementation of the Health and Body Simulation

In various embodiments, the health and body simulation can be used to model various health scenarios, which can include specific biological functions such as metabolism, inflammation, respiration, or the like. Additionally, health scenarios can relate to how physiological conditions such as a low carbohydrate diet, high exercise regimen, or the like, will globally impact the physiology of a subject.

FIG. 1 illustrates a method 1000 of simulating a biological process in accordance with an embodiment of the invention. The method 1000 begins, in block 1010, where a health scenario is selected for modeling, and, in block 1020, raw health data is obtained. Raw health data can include published clinical studies, claims data, prescription data, patient biomarkers, patient personal characteristics and lifestyle, consumer data, and the like. Additionally, sources of raw health data can include clinical data, user wearables, and the like.

In block 1030, the raw health data is cleaned and processed. For example, data cleansing can be desirable to ensure that the raw data is not inconsistent and is structured in a standardized format that can be input into the simulation module. In some embodiments, raw health data can be cleaned by a script that removes incomplete/incorrect data in order to produce a clean data set.

In block 1040, a determination is made whether the health data is sufficient to model the selected health scenario. For example, data can be considered complete if all the information to be supplied to the model is present in, or can be obtained from the provided health data. If the health data is not sufficient, then the method 1000 continues, to block 1050, where filler health data is obtained (or an attempt is made to obtain such filler health data). For example, when modeling a specific patient, health data about that patient may be provided, but such data may not be sufficient to properly setup the body model as described herein. In such cases, using information about the user, demographic or other such population or study data can be used to fill in missing data with data that is intended to represent the patient.

Similarly, in embodiments where a specific population of individuals is being modeled and data from this specific population is provided, filler-data can be data from a similar population that is intended to represent the specific population that is being modeled. In some embodiments, proprietary data can be obtained from private sources, such as commercial companies, hospitals, insurers, or the like. Public data sets can come from online sites, public feeds, published studies, government census data, and the like. Portions of these datasets can be used to fill in any missing biomarkers or characteristics needed to provide inputs to setup a given modeling task or scenario.

In block 1060, a determination is made whether the current set of health data (including filler data) is sufficient to model the health scenario, and, if not, an error is indicated in block 1070. However, if the health data is sufficient to run the health scenario, the method 1000 continues, to block 1030, where the data is again cleaned and processes if necessary.

Figure 2:
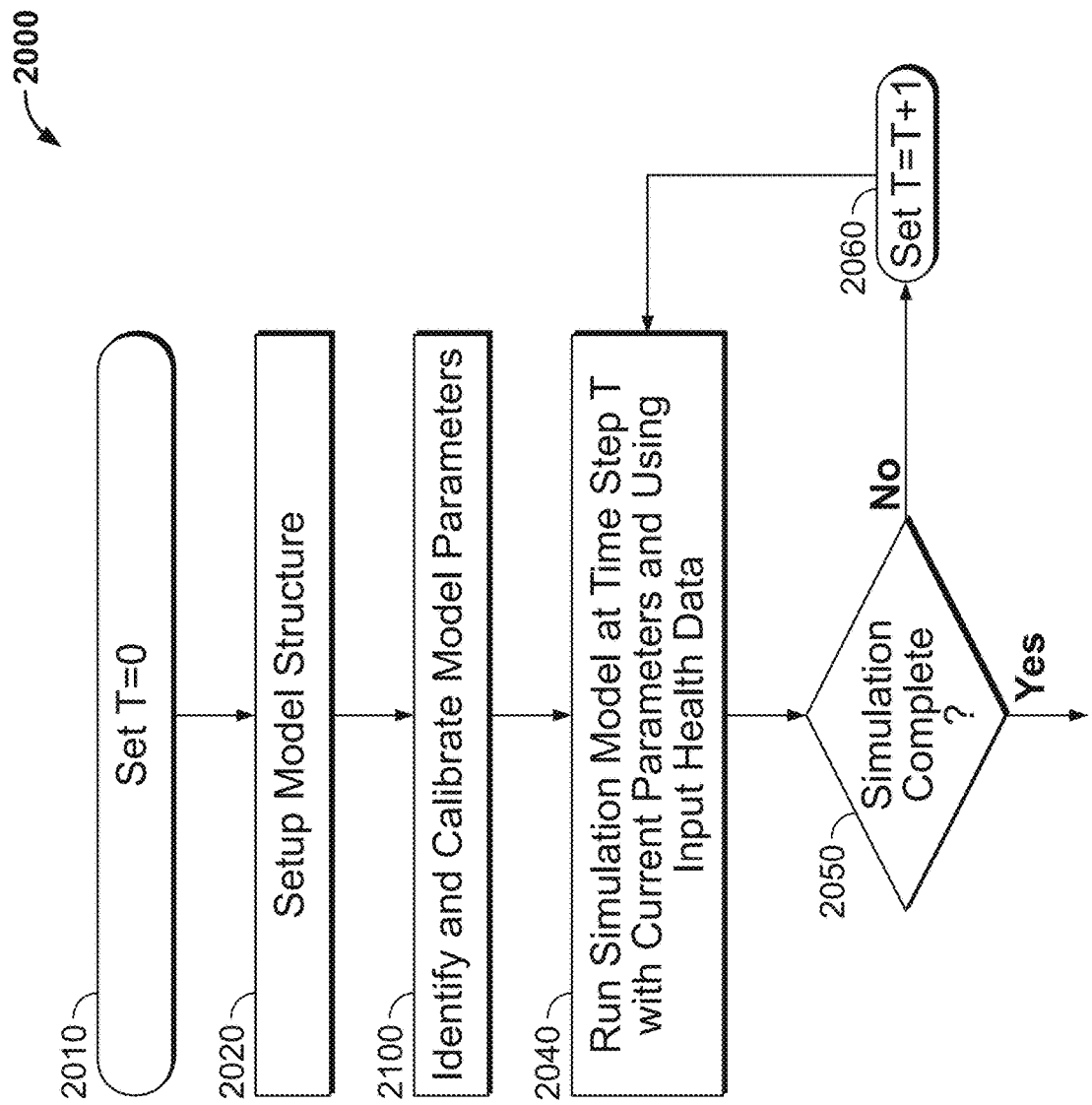
FIG. 2 is an exemplary flow chart illustrating an embodiment of a method for setting up and running a simulation model for a health scenario in accordance with the method of FIG. 1.

Returning to block 1040, if the set of health data is sufficient to run the selected health scenario, the method 1000 continues, to block 2000, where a simulation model for the selected health scenario is run as described herein and shown in FIG. 2. In block 1090, the simulation results are presented. For example, results can include suitable results data including body weight, insulin resistance, time to diabetes onset, progression of diabetes past onset, responsiveness to drugs and/or lifestyle changes (e.g., diet and exercise), time course of pancreatic dysfunction, time to need for pancreatic transplant, and the like.

FIG. 2 illustrates an exemplary method 2000 for setting up and running a simulation model for a health scenario. The method 2000 begins in block 2010 where variable T is set to 0, and, in block 2020, the model structure is setup. In various embodiments, the model structure can be a combination of biological functions that is necessary to generate the desired results for a health scenario. The model structure can be determined based on the health scenario that is initially selected (e.g., in block 1010 of FIG. 1). Setting up a model structure can comprise selecting one or more modules and/or one or more connections between modules. In some embodiments, such modules and connections can be individually selected and configured. In other embodiments, selected health scenarios can be associated with a default set of selected modules and/or connections, which may or may not be modified if desired.

The method 2000 continues to block 2100, where model parameters are identified and calibrated as described in more detail herein. In block 2040, the simulation model is run at the current time step T with current health parameters and the current set of health data. In block 2050, a determination is made whether the simulation is complete, and, if not, the method 2000 continues, to block 2060, where variable T is incremented, and the method 2000 cycles back to block 2040. For example, as discussed herein, a health scenario can be run over a selected time interval with selected time steps.

In various embodiments, time interval and/or time steps can be in seconds, minutes, hours, days, weeks, months, years, decades, or the like. For example, the time interval can be forty years with a time step of three months. In various embodiments, desired time intervals can be either based on clinical guidelines, extrinsic economic factors, or the like.

When running a health scenario, changes in each module can affect other modules as data is passed to/from the modules. Accordingly, as the variables of a given module change and affect other modules or the module is affected by other modules, the processes of a body can be simulated.

Figure 3:
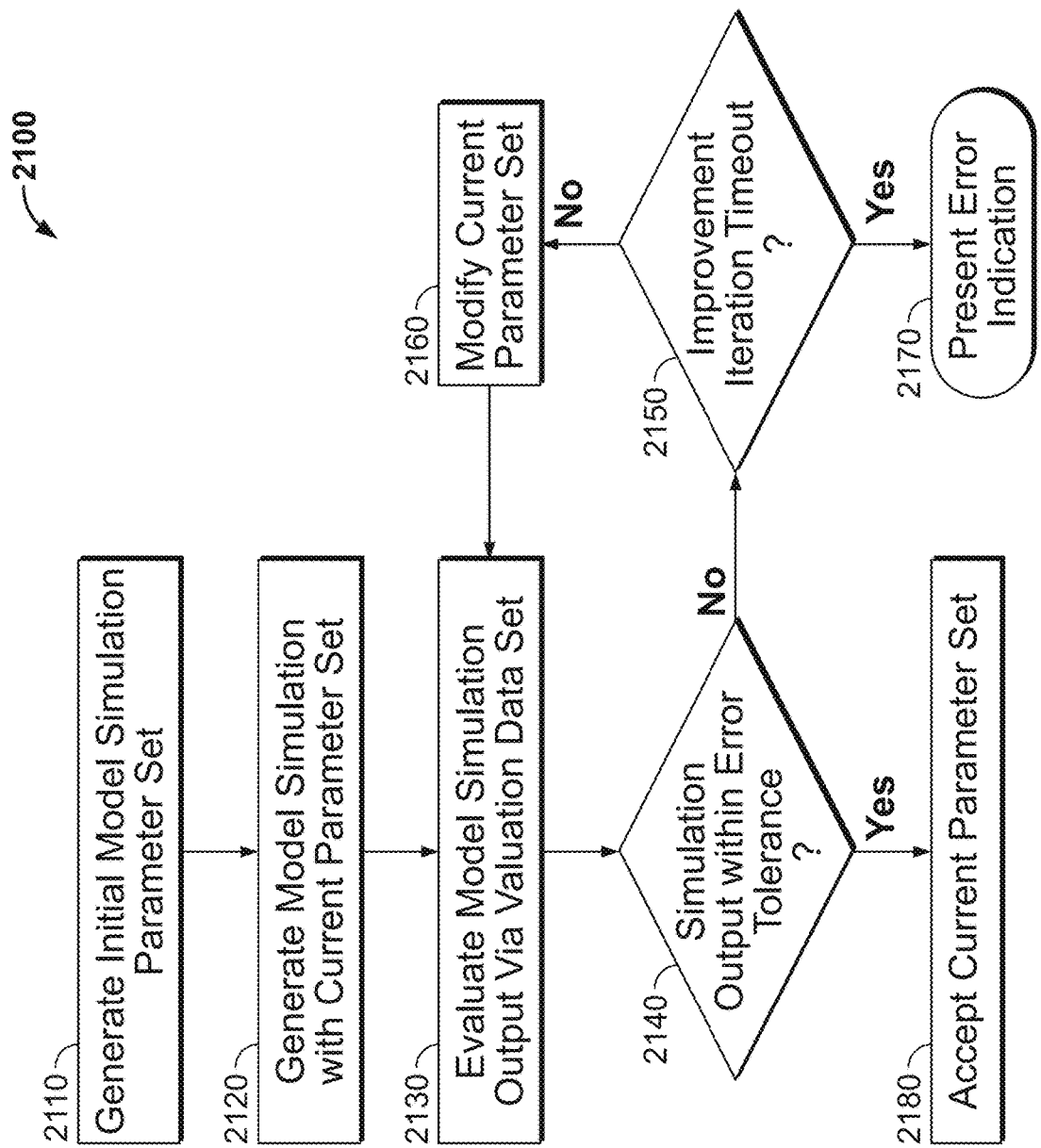
FIG. 3 is an exemplary flow chart illustrating an embodiment of the method for calibrating a model simulation in accordance with the method of FIG. 2.

FIG. 3 illustrates the exemplary method 2100 (shown in FIG. 2) for calibrating a model simulation in further detail. The method 2100 begins, in block 2110, where an initial model simulation parameter set is generated. In various embodiments, parameters are numerical quantities (e.g., time-independent constants), which are used in mathematical equations that describe relationships of system variables to inputs or relationships between system variables. For example, the rate at which glucose is converted to glycogen in muscle can be proportional to the concentration of glucose in muscle. The proportionality constant, say k, relating the rate of conversion to glucose concentration is an example of a parameter. Each module and the components and connections thereof can include one or more parameter. In some embodiments, numerical values of some of these parameters may be exactly known, while others may be unknown.

However, even if parameters such as k are not uniquely known, numerical ranges over which such parameters could vary can be determined. For example, while the value of k may not be precisely known, an initial estimate could suggest that k lies between 10 and 50 seconds$^{-1}$. Thus (10, 50) seconds' can be an initial estimate of the range of parameter k.

In some embodiments, an initial estimate of such a range can be obtained from scientific literature, or other suitable source, in various ways. For example, previously published models of similar systems may suggest likely ranges of parameters, or the like. Accordingly, data observed in experimental studies related to a given process can be examined and initial ranges can be estimated based on the results of such studies. In the absence of any information from the literature or other sources, ranges can be empirically determined by iterative trials, a random guess can be made, or a default value can be used.

In various embodiments, a parameter estimation process can be utilized to estimate unknown parameters. For example, an initial guess can be generated by randomly choosing a number lying within a range determined for a parameter as described above. Continuing the example above, parameter k, whose range is estimated to be (10, 50) seconds$^{-1}$, an initial guess could be 35.47 seconds$^{-1}$. In some embodiments, a computer algorithm can pick this random value in the specified range in an unbiased manner. Similarly, a set of initial guesses for other unknown parameters can be generated until all parameters of the model have been assigned numerical values, either as an initial guess, as a parameter with known value, or the like.

In block 2120, a model simulation is generated with the current parameter set. For example, once the model is uniquely defined by the values assigned to parameters, the model can be simulated by solving the set of differential, algebraic equations, or the like, that defines the model as embodied in the modules 230 and interconnections of the modules 230 that describe the biological system being modeled.

In various embodiments, a simulation result can be a matrix of numbers describing time-dependent changes in the values of all the variables comprising the model. The entire matrix, or parts of it, can be presented visually or in any other suitable form such as a table, line curve, bar graph, or the like. For example, after simulating the model with k=35.47 seconds$^{-1}$, a matrix of numbers describing the dynamics of all variables in the model could be obtained. From this matrix, it can be possible, for instance, to select the rows or columns containing information about the dynamics of concentration of blood glucose over time (e.g., denoted by the variable G(t)).

In block 2130, output from the model simulation is evaluated via a training data set, and, in block 2140, a determination is made whether the simulation output is able to replicate the values of the corresponding variables in the training data set within a desired error tolerance. In various embodiments, training data can comprise a data set obtained from scientific literature, publicly available databases, a source that contains experimentally measured data about the variables present in the model, or the like. Accordingly, the purpose of a training data set can be to provide data that can be used to estimate the parameters of the model.

For example, among other variables, a model can simulate the concentration of blood glucose (represented by G(t) as discussed above). Assuming the model is being trained to represent a healthy individual, an example of a training data set could be experimentally measured concentrations of blood glucose in several healthy individuals over a period of time.

The variables of a given model can correspond to variables available in the training data, which can be isolated. For example, time dependent blood glucose concentration, G(t), can be extracted from the complete model output as described above. The numerical values of blood glucose as predicted by the model can then be compared with the numerical values of blood glucose available in the training data. A numerical score or fitness score can be assigned to the model depending on how well the model simulated values match the training data. For example, in some embodiments, the fitness score can be designed to be low for a good match and high for a poor match between model output and training data.

To determine whether the fitness score is acceptable, the fitness score can be compared to a pre-determined threshold value. For example, if the fitness score is below this threshold, the model can be deemed to describe the training data set well, and the method 2100 continues, to block 2180, where the current parameter set is accepted. In various embodiments, the tolerance limit can be a number whose value is chosen on a case-by-case basis using expert judgment.

For example, in a particular calibration run the tolerance limit could be ten. If the fitness score is less than or equal to ten, the parameter values are accepted as a good estimate. If the fitness score is greater than ten, the parameters are refined further, and the method 2100 continues to block 2150, where a determination is made whether improvement iteration has timed out. For example, if the parameters are changed and refined over a large number of iterations but do not converge on values that create an output within a desired error tolerance, the method 2150 can present an error indication, in block 2170. In such a case, a user can have an opportunity to modify the parameters, change the error tolerance, change the input data, change the model connections or module configuration, or make other changes that might generate a suitable simulation that would produce an output that is within a desired error tolerance.

However, returning to block 2150, if the improvement iteration has not timed out, the method 2100 continues, to block 2160, where the current parameter set is modified. Accordingly, in various embodiments, the process of calibration can be an iterative one, and a new set of candidate parameter values can be generated in each iteration. Such candidate values can result in an increased, decreased, or unchanged fitness scores, thus making the simulation less, more or equally accurate over the iterations. In various embodiments, the training data remains the same over each iteration/simulation. In some embodiments, successive iterations are compared based on their fitness scores, and the change in fitness score can be used to determine how to modify the parameters in a successive iteration.

In various embodiments, a perturbation factor can be added to the variables in some iterations. For example, in some embodiments, if a subsequent iteration has reduced fitness, un-changed fitness or increased fitness, a perturbation factor can be added. Such a perturbation factor can change over iterations or remain the same. For example, if adding the perturbation makes the simulation output less accurate or unchanged, the perturbation factor can be adjusted. In some embodiments, direction and/or magnitude of the perturbation factor can be determined via an algorithm or by a human operator.

Testing and Selection of Intervention Programs Using the Health and Body Simulation In various embodiments, it can be desirable to test and identify health interventions that can improve the health of a given patient or population. For example, population health prediction continues to be important for employers, insurance companies, wellness organizers, or any organization holding risk in the health ecosystem. Health organizations that hold risk continue to introduce new and innovative methods to nudge individuals towards a healthier state. Accordingly, in various embodiments, a body simulation model can be used to quantify the future health state of an individual or population based on current available data, and selecting a suitable health intervention can be based on a desired health outcome. For example, a desired outcome can include reduction in fasting glucose, improved results from a glucose tolerance test, weight loss, chronic disease (e.g., diabetes) prevention, and the like.

Figure 4:
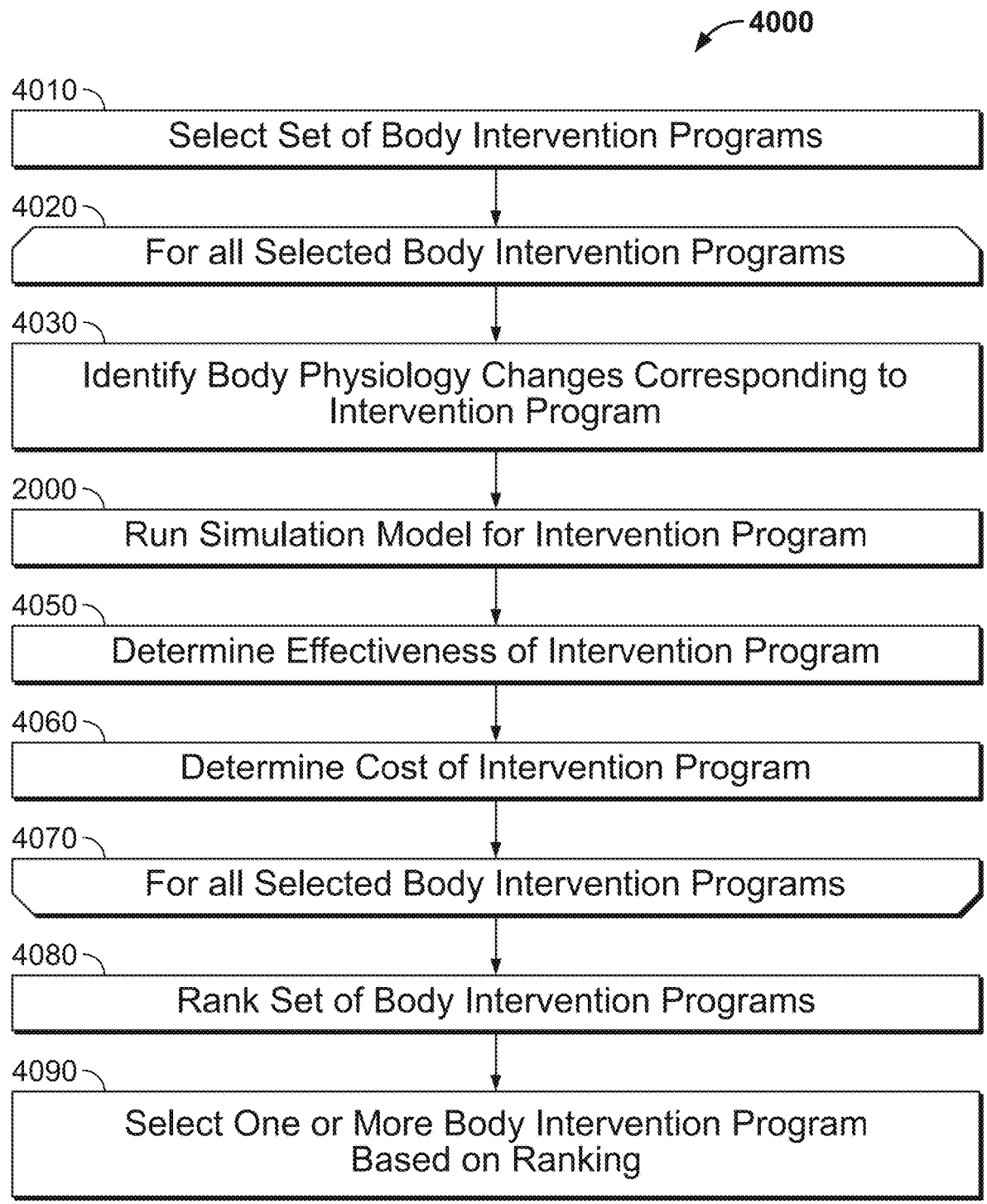
FIG. 4 is an exemplary flow chart illustrating an embodiment of a method of testing and selecting body intervention programs.

FIG. 4 illustrates an exemplary method 4000 of testing and selecting body intervention programs. The method 4000 begins, in block 4010, where a set of intervention programs is selected. For example, based on the desired outcome, a list of types of intervention programs can be generated that could potentially achieve the desired outcome. In one example, interventions related to diabetes prevention may include a diet control only intervention, activity change only intervention, or a diet and activity change intervention. In various embodiments, intervention programs can include increased and/or decreased cardiovascular training, resistance training, sleep, macronutrient specific diets, or the like to deliver the optimal outcomes with minimal interventions. In some embodiments, an intervention program can include changes in diet, drug use, smoking, stress, or the like.

For example, different intervention programs can include different consumption rates of different macronutrients such as carbohydrates, fat, cholesterol, and the like. In various embodiments, alternative intervention programs can include several values for a given change (e.g. 5%, 10%, 15% change in carbohydrate intake). Additionally, some intervention programs may have changes in a plurality of such health or body related variables or changes.

In intervention looping block 4020, a loop begins for each of the selected body intervention programs, and, for each selected body intervention program, the method 4000 continues to block 4030, where body physiology changes corresponding to the intervention program are identified by simulating the intervention. In various embodiments, a given intervention program can change input data for a given model and/or can change the parameters of the model. For example, for diet related interventions such parameters can include modifying the intake of protein, carbohydrate, fat, fiber, or the like. Additionally, smaller scale nutritional information such as specific types of carbohydrates, fats, and protein can also be used in some embodiments. Additionally, in further embodiments, nutritional information from consumer retail products can be used.

In block 2000, a simulation model is run for the intervention program and, in block 4050, an effectiveness of the intervention program is determined. For example, effectiveness can be determined based on a change in a specific clinical marker of interest, including A1c levels, or risk of diabetes, body weight, or the like. If the desired health outcome was prevention of onset of diabetes over the next ten years, then a model output for a specific intervention can be whether there is onset of diabetes over the next ten years or a percent chance that onset of diabetes will occur.

Health-effectiveness can be determined by the degree of change in the model output of interest (e.g., serum HbA1c level) due to changes introduced by the intervention. For example, while multiple interventions could prevent onset of diabetes, one intervention could produce a larger difference than the other (e.g. one intervention brings the final serum HbA1c level to just below 6.5 while another brings it closer to 5.7 (pre-diabetes onset)). Examples of not being effective would be an insignificant or insufficient reduction the serum HbA1c levels.

In block 4060, the cost of the intervention program is determined. For example, the cost of a given intervention program can be estimated in one of several possible ways, including calculating cost of a medication over a time period, cost of health care services over a time period, cost of a gym membership of the time period, and the like. In various embodiments, program cost can be computed through research of comparable intervention plans.

In block 4070, the loop for all selected body intervention programs ends. In other words, once all intervention programs have been evaluated, the method 4000 continues, to block 4080, where the set of body intervention programs is ranked. Such ranking can be done in one of many suitable ways. For example, in various embodiments, cost and effectiveness of a given program can be assigned different weighting factors and a rank could be generated by combining the weighted cost and weighted effectiveness. In some embodiments, cost may not affect an intervention unless cost reaches a given threshold (e.g., an insurance limit). In other embodiments, cost and effectiveness can receive similar weighting in generating a rank because finding the lowest cost, but most effective solution may be desirable. In further embodiments, a cost/benefit analysis can include consideration of cost to implement intervention and cost associated with health at end of intervention and projected future health state of the population or patient.

In block 4090, one or more of the body intervention programs are selected based on rank. For example, in some embodiments, the top-ranked program can be selected. In other embodiments, a plurality of top-ranked programs (e.g., the top three) can be selected.

Diabetes Model

Simulation modeling of diabetes and related physiological parameters is described in detail here to illustrate the principles of the invention outlined above. It is understood that these principles may be applied to any simulation described above.

Diabetes was elected as the simulation to exemplify the principles of this invention because it is a huge burden on the US healthcare economy costing $174 billion per year (estimates from 2007). The latest reports from the CDC project that the prevalence of diabetes is expected to grow from current estimates of around 14% to 25-28% in 2050. A closer look shows that the two primary reasons for this projected increase in diabetes prevalence are: (a) the growth of minority communities where prevalence is particularly high due to factors including genetic predispositions and lifestyle choices and (b) increased life expectancy due to the advancement of medical care and new drugs, allowing diabetic patients to live longer than before. It is well established in literature that diabetes significantly increases the risk for several co-morbidities that include cardiovascular disease, nephropathy, neuropathy, risk of amputation etc. Hence, diabetes is not just a healthcare problem; it is an economic problem.

Studies on larger populations of diagnosed diabetic patients found that 57.5% of the subjects had uncontrolled or unmanaged HbA1c (>9%). There is a need for improved care for diagnosed diabetes through a combination of pharmacological and lifestyle interventions such that HbA1c levels are better controlled. However, when it comes to diabetic patients there seems to be confusion regarding the goal for a lifestyle intervention. In the pre-diabetic population, it has been shown that a body-weight reduction of greater than 6% leads to significant reduction in risk for onset of diabetes. However, it remains unclear whether the goal for lifestyle interventions should be to achieve weight loss, increased physical activity, or improved HbA1c target.

Previous mathematical models of human metabolism have focused on energy balance in the body. The manifestation described here primarily focuses on mass balance of three major macronutrients in the body—carbohydrates, protein and fat. It is assumed that the changes in energy consumption by processes other than aerobic respiration (e.g., gluconeogenesis) are small and can be ignored compared to changes in energy requirements for regular body functions and physical activity. Within the scope of this assumption, the model also balances the energy of the entire system. Decreases in energy expenditure (e.g., due to reduced physical activity), keeping the intake of macronutrient the same, lead to increases in weight predominantly through an increase in fat mass.

The present disclosure is exemplified using a computational model that brings together all relevant systems from macronutrient mass balance, insulin secretion, and inflammation to develop a more comprehensive representation of the systems. The model supports the biological processes which have been implicated for the development of pre-diabetes and onset of diabetes.

Figure 5:
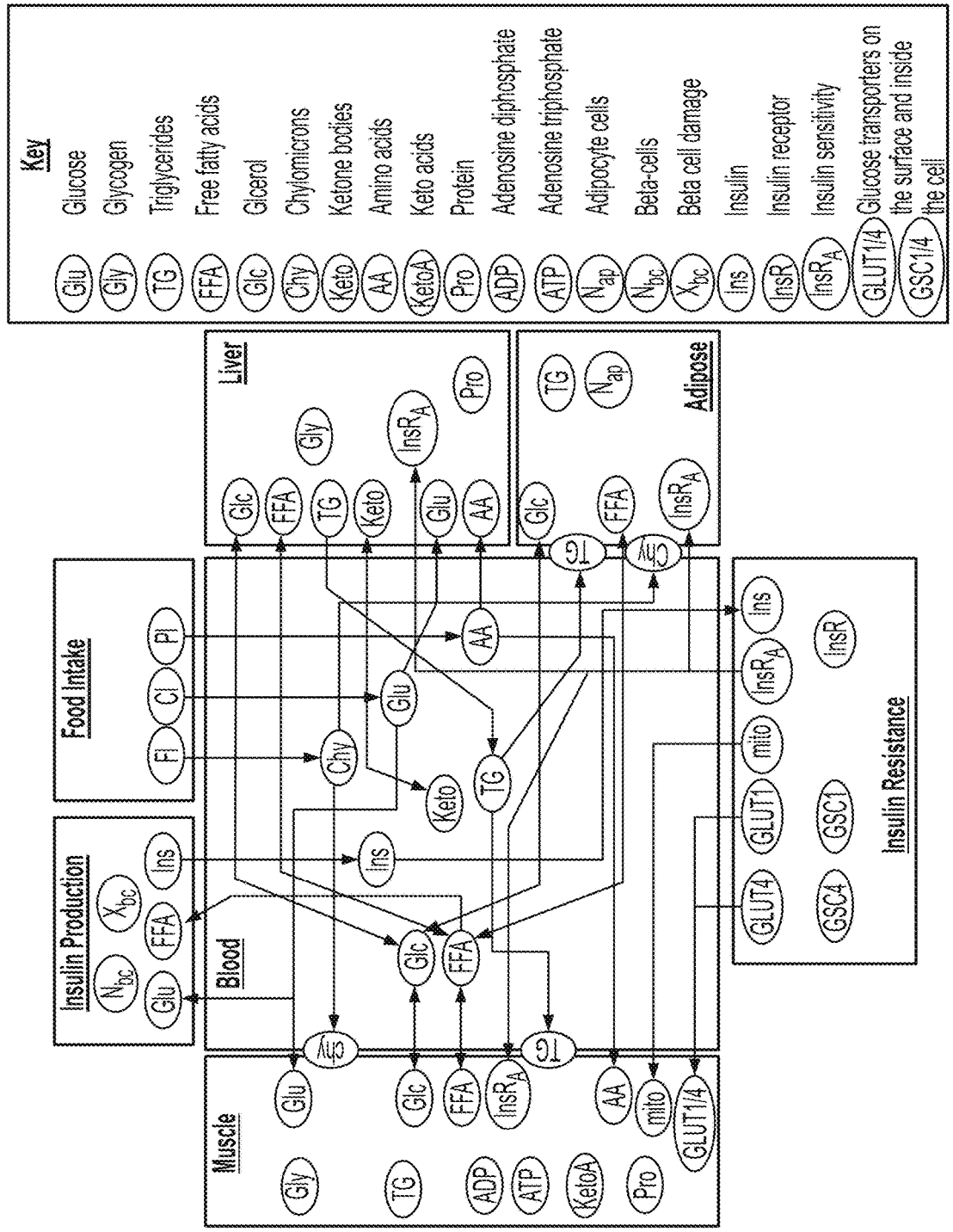
FIG. 5 is an exemplary top-down diagram illustrating an embodiment of computational modules which support the biological processes implicated for the development of pre-diabetes and onset of diabetes.

The computational model of diabetes is a top-down designed model composed of 6 compartments that together reproduce the major biological processes which lead to the development of insulin resistance, development of pre-diabetes, and onset of diabetes in patients (FIG. 5). The model spans 4 scales—from molecular, cellular, tissue/organ to whole-body. The model is divided into (1) a blood module, (2) a metabolism module that has submodules of (i) muscle, (ii) liver, and (iii) adipose tissue, (3) an insulin sensitivity/resistance module, and (4) an insulin production module. These modules and submodules are represented in FIG. 5. The scientific reasoning behind the choice of these specific compartments is driven by the ability of the minimal model to reproduce macronutrient metabolism as it pertains to weight gain, development of insulin resistance and irreversible progression to diabetes. Each of the modules and submodules is described in more detail below.

1.0 Blood Module

Figure 6:
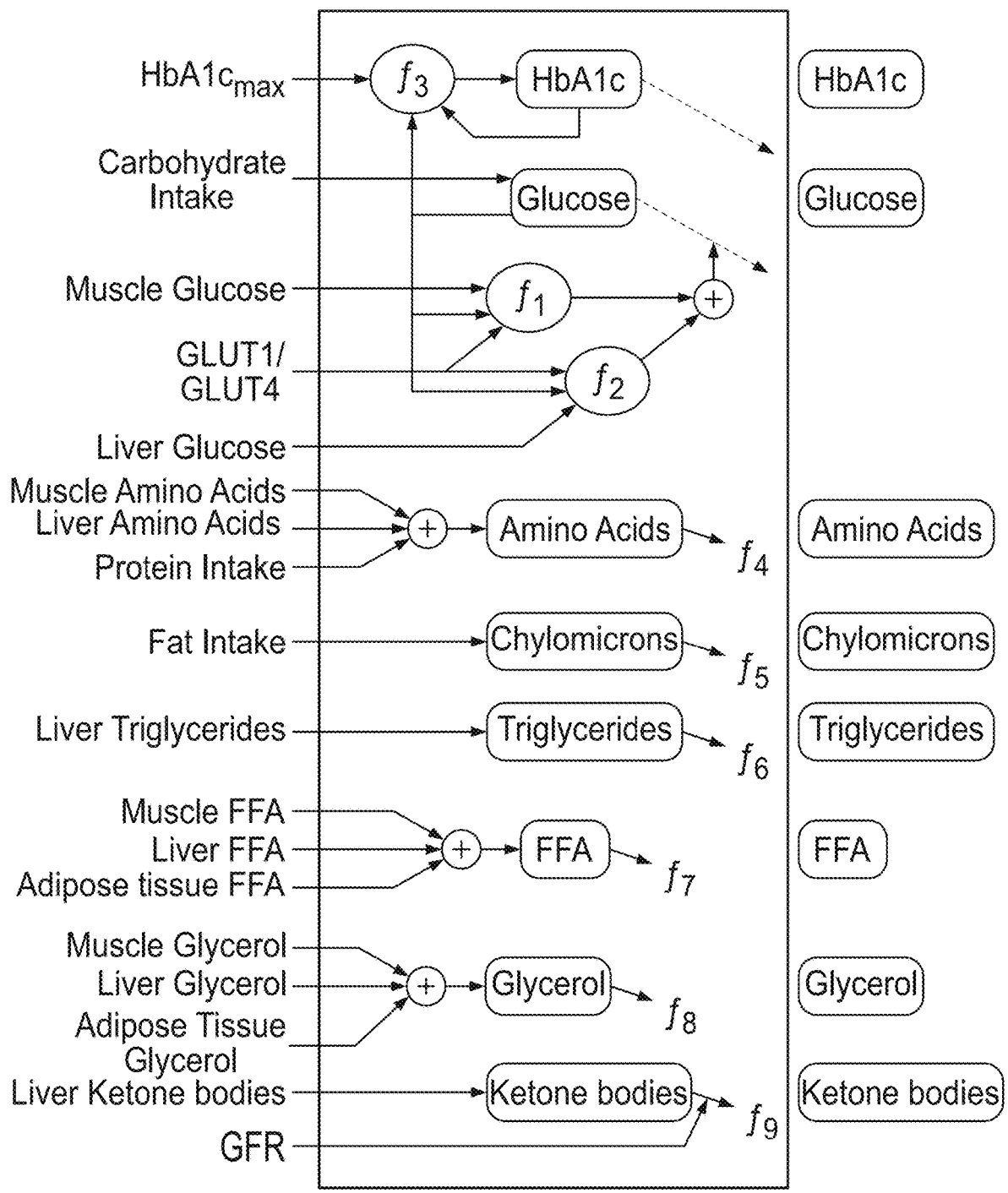
FIG. 6 illustrates one exemplary embodiment of the blood module of FIG. 5.

In various embodiments, the blood module can be configured to receive, transport, and deliver macronutrients, lipids, insulin, hormones (leptin, ghrelin, glucagon, testosterone, estrogen, etc.), cell-signaling proteins (adipokines, cytokines, etc.), immune cells (leukocytes, lymphocytes, etc.), neurotransmitters (epinephrine, norepinephrine, acetylcholine, etc.), and the like, between the other modules described below. An example embodiment of a generic blood module is illustrated in FIG. 6.

In some embodiments, the blood module does not contain any internal dynamics but is merely responsible for the communication of the concentration of various substances between the various other modules.

In some embodiments, the blood module can relate the dynamics of the model to clinical measurements. For example, one way the health of a person is measured is by drawing blood in a lab and measuring its content of lipids, hormones, glucose, etc. The blood module can provide for a virtual blood draw to be generated from the model and can be used to calibrate the model to clinical blood sample data.

As discussed herein the blood module can be connected to various other modules, including the metabolism module, the insulin production module, the insulin sensitivity module, and/or any other modules that may be included in the model. In various embodiments, the blood component also receives data regarding consumed dietary macronutrients and distributes such data to the appropriate modules.

One specific implementation of the blood module is illustrated in FIG. 6. In this implementation, the blood compartment is central to the simulation and connects the remaining modules and sub-modules. FIG. 6 illustrates the inputs and calculations of each of the blood levels that may be estimated over time. Inputs into the blood compartment model include:

---

Muscle Glucose
Free Fatty Acids (FFA)
Glycerol
Free amino acids
Liver Glucose
Glycerol
Triglycerides
Adipose Tissue Free Fatty Acids
Carbohydrate intake
Fat intake
Protein intake

---

The blood compartment integrates and calculates an estimate, over time, of the following concentrations in blood:

---

HbA1c
Serum Glucose
Free amino acids
Chylomicrons
Triglycerides
Free Fatty Acids (FFA)
Glycerol
Ketone bodies

---

The blood compartment also interfaces with the terms related to the ingestion of food and delivery of macronutrients to the blood supply. For steady-state behavior, the process of ingestion, digestion and absorption of food has been abstracted into direct delivery of the relevant forms of the macronutrients in the blood compartment:

1. Carbohydrate consumption is represented as a flux of glucose into blood.
2. Fat consumption is represented as a flux of chylomicrons into blood.
3. Protein consumption is represented as a flux of amino acids into blood.

Transport of glucose from blood to tissues (muscle and liver) are represented as the function $f1$ and $f2$. The transport of most species are represented as 1st order processes which are represented as functions. The process of glycosylation of hemoglobin is incorporated in blood. The glycosylation process ($f3$) includes an amount of hemoglobin that can be glycosylated, which produces an upper bound on the process and concentration of glycosylated hemoglobin (HbA1c). Detailed descriptions of the functions in the blood module are provided below.

TABLE 1.0

| Reaction | Equation |
| --- | --- |
| $f_1$ | $-((k_{glu_b,muscle,GLUT1} * C_{GLUT1} + k_{glu_b,muscle,GLUT4} * h(C_{GLUT4})) * (C_{glu,b} - C_{glu,muscle}))/(V_b + V_{ECF})$ |
| $f_2$ | $-((k_{glu_b,liver,GLUT1} * C_{GLUT1} + k_{glu_b,liver,GLUT4} * h(C_{GLUT4})) * C_{glu,b})/(V_b + V_{ECF})$ |
| $f_3$ | $k_{glu,hba1c} * C_{glu,b} * (C_{hba1c\_max} - C_{hba1c,b})$ |
| $f_4$ | $-(k_{aa_b,muscle} * C_{aa,b} + k_{aa_b,liver} * C_{aa,b})/V_b$ |
| $f_5$ | $-(k_{chy_{lpa,muscle}} * C_{chy,b} + k_{chy_{lpa,adipose}} * C_{chy,b})/(V_b + V_{ECF})$ |
| $f_6$ | $-(k_{tg_{lpa,adipose}} * C_{tg,b} + k_{tg_{lpa,muscle}} C_{tg,b})/(V_b + V_{ECF})$ |
| $f_7$ | $-(k_{FFA_b,muscle} * C_{FFA,b})/(V_b + V_{ECF})$ |
| $f_8$ | $-(k_{glc_b,liver} * C_{glc,b} + k_{glc_b,muscle} * C_{glc,b})/(V_b + V_{ECF})$ |
| $f_9$ | $(k_{aa_{muscle,b}} * C_{aa,muscle})/V_b$ |
| h(X) | $\dfrac{d}{1 + ae^{-c*(X-b)}}$ |

2.0 Metabolism Module

In one embodiment, the metabolism module is based on a metabolic model described by Kevin Hall in, "Predicting metabolic adaptation, body weight change, and energy intake in humans," Am. J. Physiol. Endocrinol. Metab., 298:E449, 2010, which is hereby incorporated by reference herein in its entirety for all purposes. For example, Hall derives a differential equation based model that tracks the time evolution of stored body protein (P), fat (F), glycogen (G) and extracellular fluid (ECF) in response to diet, exercise and current body weight (BW). In support of tracking these macronutrient variables, the metabolic model has explicit representations of: resting metabolic rate; total energy expenditure; gluconeogenesis; glycogenesis; glycogenolysis; ketogenesis; lipolysis; re-esterification; de novo lipogenesis; proteolysis; glycolysis; and macronutrient oxidation rates.

In some embodiments, the metabolism module is subdivided into muscle (2.1), liver (2.2), and adipose tissue (2.3) sub-compartments. In such embodiments, each sub-compartment can perform parallel metabolism calculations containing different collections of processes mentioned above (e.g., macronutrient oxidation rates may only be present in the muscle tissue in some embodiments, or the like). The sub-metabolism models in each metabolism sub-compartment can be specialized by containing different parameters to represent the differences in the sub-compartment metabolic processes (e.g., gluconeogenesis happens primarily in the liver while macronutrient oxidation happens primarily in the muscle, etc.). In various embodiments, each sub-component of the metabolism module component can exchange glucose data, free fatty acids (FFA) data, ketone bodies data, and protein data back and forth with the blood module (1.0).

In some embodiments, such a metabolism model can be beneficial because there are only a few parameters to be fit to have the model represent an individual. Specifically, the model requires initial conditions for P, F, G, ECF, and BW, and remaining parameters can be fit to the following data: baseline fat intake; baseline protein intake; baseline carbohydrate intake; and basal metabolic rate (BMR).

2.1 Metabolism Module—Muscle Submodule

Figure 7:
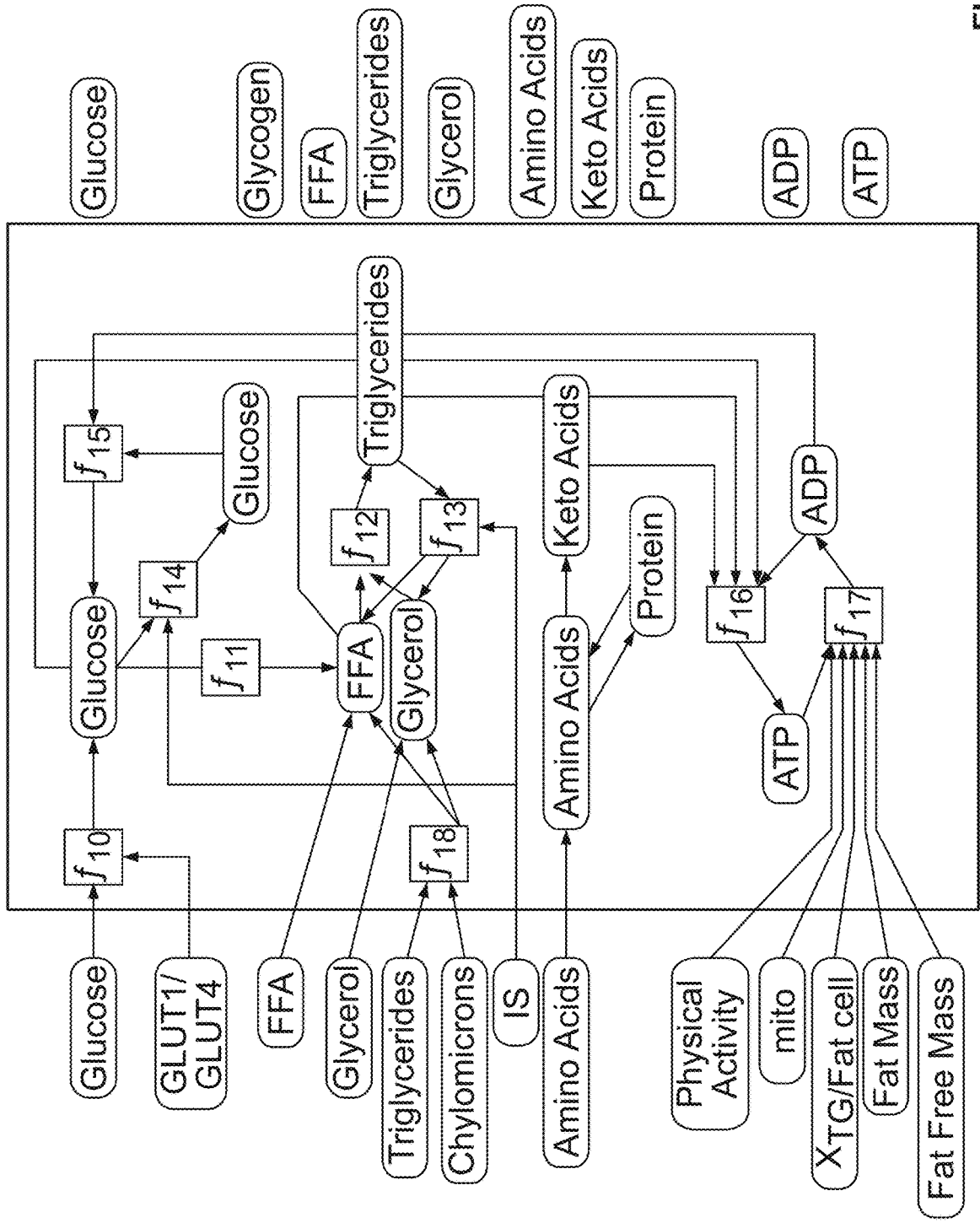
FIG. 7 is an exemplary diagram illustrating one embodiment of the muscle subcomponent of the metabolism module of FIG. 5.

The muscle compartment represents an abstraction of all major tissues in the body other than liver and adipose tissue, which have been distinguished in the model as their own separate compartments. The muscle compartment incorporates the transport of all 3 major macronutrients from blood e.g. uptake of free fatty acids (FFA) from chylomicrons and triglycerides ($f$ 18), as shown in FIG. 7. The compartment further represents the metabolic processes for the interconversion between different species e.g. de novo lipogenesis (DNL) ($f$ 11), glycogenesis ($f$ 14), glycogenolysis ($f$ 15), lipolysis ($f$ 13). The compartment incorporates the oxidation of macronutrients, phosphorylation of adenosine diphosphate (ADP) ($f$ 16) to adenosine triphosphate (ATP) and the hydrolysis of ATP ($f$ 17) to release energy. The model assumes that the concentration of species in the interstitial space (ISF) and inside the cell is in rapid equilibrium. Hence concentrations represent the concentrations of species inside the cells in many cases. The details of the specific processes are below.

GLUT1/GLUT4 Mediated Glucose Transport

The transport of glucose into the cells of the muscle compartment is represented as a simple gradient flow of glucose. However, the permeability of the gradient process is defined as a non-linear function ($f$ 10) of the concentrations of both GLUT1 and GLUT4 transporters on the cell surface. GLUT1 and GLUT4 are described in the insulin resistance module.

De Novo Lipogenesis (DNL)

While the liver is the main site for DNL, in conditions of excess glucose inside the muscle compartment, there is conversion to fat in this compartment as well. The conversion of glucose to fat is modeled as a Hill function ($f$ 11) such that significant lipogenesis only happens in conditions of significant excess of glucose over steady-state conditions.

Glycogenesis/Glycogenolysis

The model represents the dynamic equilibrium between glucose and glycogen in the muscle compartment. In the model, glycogen is made from four glucose molecules and this stoichiometry is maintained everywhere. Any excess glucose is converted to glycogen and vice versa. The rate of glycogenesis ($f$ 14) is proportional to the concentration of glucose in the tissue, insulin sensitivity (IS) and the remaining availability for glycogen storage. There is a maximum amount of glycogen that muscle cells can store which is incorporated into the model and this term constrains the glycogen concentration to that maximum amount. The glycogenolysis process ($f$ 15) is proportional to glycogen concentration but is further controlled by the energy state of the muscle cells represented in this term as the ATP/ADP ratio.

Fatty Acid Uptake

Serum TGs and chylomicrons serve as the primary sources of fat to the muscle compartment. Lipoprotein lipase (LPA) hydrolyses circulating TGs and chylomicrons ($f$ 18) into FFAs and glycerol in the muscle compartment. Excess glycerol transport back into blood is represented as a first order process. There is bidirectional transport of FFAs between blood and muscle compartment. There exists a dynamic equilibrium between FFA, glycerol and TG ($f$ 12, $f$ 13) where 3 FFA molecules combine with one glycerol molecule to create one TG molecule, and this stoichiometry is preserved everywhere.

Amino Acid Uptake and Protein Metabolism

The detailed mechanistic regulation of the amount of protein mass in humans is not well understood in the literature. The amino acid fluxes in and out of the muscle compartment are represented as 1st order processes. Inside the muscle compartment amino acid and protein concentrations are in dynamic equilibrium with a stoichiometric ratio of 500. Amino acids are also converted into ketoacids for use in energy metabolism.

Macronutrient Oxidation and ATP Hydrolysis

The muscle compartment is the main site of macronutrient oxidation and ATP hydrolysis. Glucose, fat, and ketoacids fuel the ATP synthesis process in the model. The described manifestation of the model only represents aerobic oxidation of the fuels and abstracts the details of cellular respiration into a single step reaction. The rate of oxidation of all three types of fuel is proportional to the concentration of ADP and mitochondrial function (input from IR compartment). The rate of oxidation of ketoacids is directly proportional to the concentration of ketoacids in the compartments while the rates of oxidation of glucose and FFA are represented as saturable processes. The three fuels lead to the generation of different amounts of ATP and this stoichiometry is also incorporated into the equations. The stoichiometry is tuned such that the respiratory quotient is 0.85 at steady state and ketoacids contribute approximately 20% to ATP synthesis.

The hydrolysis of ATP to ADP is proportional to available concentration of ATP in the muscle compartment. However, several additional mechanisms regulate the rate of hydrolysis. The rate of ATP hydrolysis is increased with increase in fat mass (FM) and fat-free mass (FFM) and in the model the differential increase in metabolic rate is taken into account. The model differentiates between energy expenditure for regular body function and physical activity, so changes in energy expenditure due to changes in physical activity are also incorporated into the ATP hydrolysis equation. Furthermore, depending upon fat content of the fat cells—leptin mediated metabolic adaptation is simulated. All of the above mentioned factors are taken into account into the rate of ATP hydrolysis ($f$ 17).

Detailed descriptions of the functions in the muscle submodule are provided below.

TABLE 2.0

| Reaction | Equation |
|---|---|
| h(X) | $\dfrac{d}{1 + ae^{-c*(X-b)}}$ |
| $f_{10}$ | $-((k_{glu_b,muscle,GLUT1} * C_{GLUT1} + k_{glu_b,muscle,GLUT4} * h(C_{GLUT4})) * (C_{glu,b} - C_{glu,muscle}))/(V_{muscle})$ |
| $f_{11}$ | $k_{glu,ffa_{muscle}} * \dfrac{C_{glu,t}^{n_{glu,ffa}}}{C_{glu,t}^{n_{glu,ffa}} + km_{glu,ffa}^{n_{glu,ffa}}}$ |
| $f_{12}$ | $k_{ffa,tg_{muscle}} * C_{ffa,t} * C_{glc,t}$ |
| $f_{13}$ | $\dfrac{(k_{tg,ffa_{muscle}} * C_{tg,t})}{\left(1 + \left(\dfrac{IS}{kI_{lipolysis,insulin}}\right)^{n_{lipoysis,insulin}}\right)}$ |
| $f_{14}$ | $k_{glu,gly_{muscle}} * (C_{gly,muscle}^{max} - C_{gly,t}) * C_{glu,t} * IS$ |
| $f_{15}$ | $k_{gly,glu_{muscle}} * \dfrac{C_{gly,t}}{1 + \left(\dfrac{r_{ATP,ADP}}{kI_{dg,atp}}\right)^{n_{dg,atp}}}$ |
| $f_{16}$ | $\left(k_{ffa,adp} * \dfrac{C_{ffa,t}}{C_{ffa,t} + km_{ffa,adp}} + k_{ketoa,adp} * C_{ketoa,t} + k_{glu,adp} * \dfrac{C_{glu,t}}{C_{glu,t} + km_{glu,adp}}\right) * C_{adp,t} * C_{mito}$ |

TABLE 2.0-continued

| Reaction | Equation |
|---|---|
| $f_{17}$ | $k_{atp,adp} * C_{atp,t} * (1 + \alpha_{RER,FFM} * (FFM - FFM_0) + \alpha_{RER,FM} * (FM - FM_0)) * RMR_{PAadjustment} * RMR_{BWadaption}$ |
| $f_{18}$ | $(k_{tg,lpa_{muscle}} * C_{tg,b} + k_{chy,lpa_{muscle}} C_{chy,b}) * (1 + \alpha_{lpa,ampk})/(V_{muscle})$ |
| mROS | $k_{etc,leakage} f_{16}$ |

2.2 Metabolism Module—Liver Submodule

Figure 8:
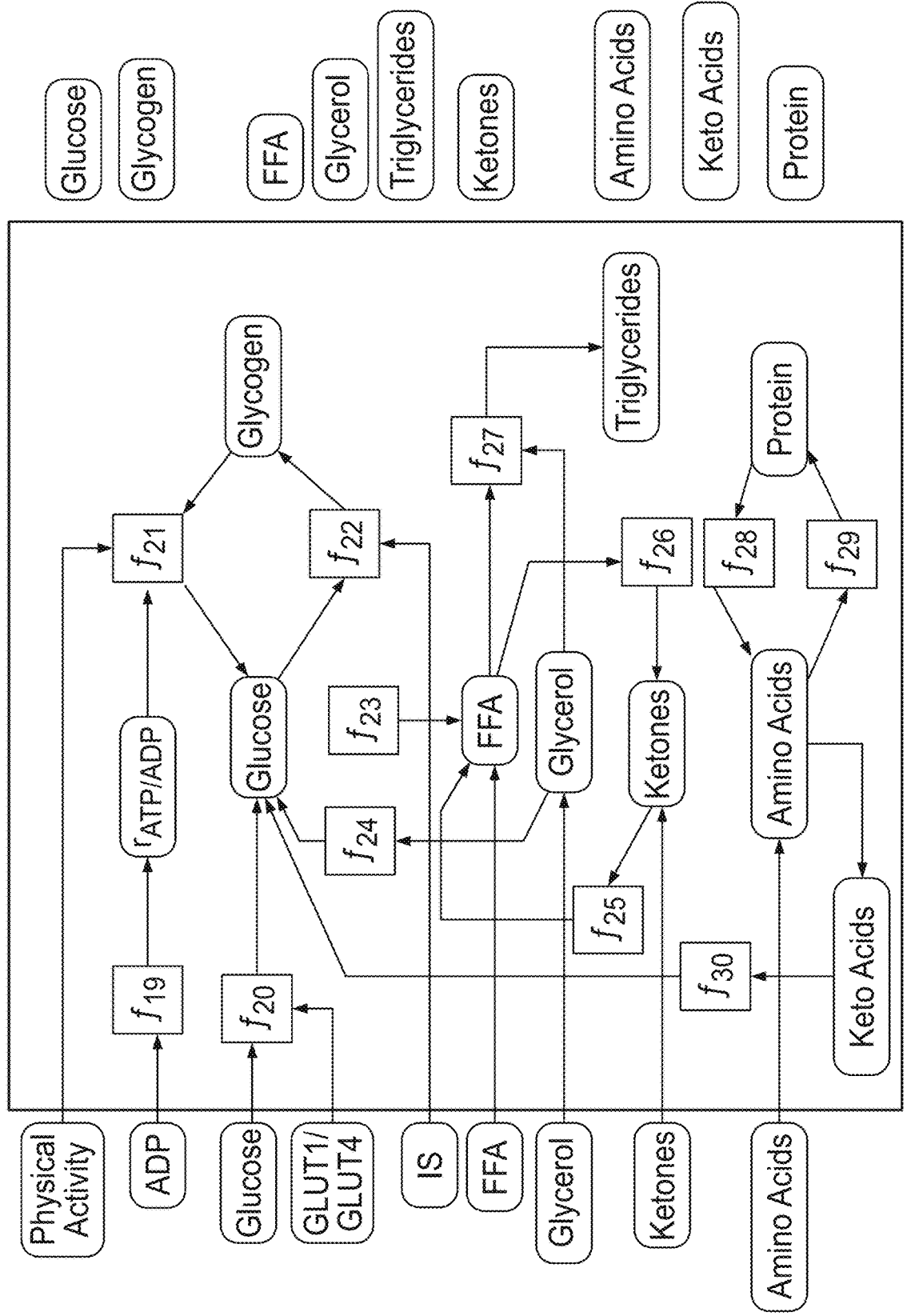
FIG. 8 is an exemplary diagram illustrating one embodiment of the liver subcomponent of the metabolism module of FIG. 5.

Liver is another major compartment involved in macronutrient metabolism. Many of the processes incorporated in the muscle compartment are also present in the liver compartment (FIG. 8) and only the differences have been described in detail. FIG. 8 illustrates the inputs and calculations of each of the blood levels that may be estimated over time. Inputs into the liver compartment model include:

Serum Glucose
Free Fatty Acids (FFA)
Glycerol
GLUT1/GLUT4
IS
Ketone Bodies

GLUT1/GLUT4 and IS are described in in the insulin resistance module.

The liver compartment integrates and calculates an estimate, over time, of the concentrations of following in liver:

Glycogen
Liver Glucose
Free Fatty Acids (FFA)
Triglycerides
Glycerol
Ketone bodies GLUT1/GLUT4 Mediated Glucose Transport The mechanism of glucose uptake by the liver compartment ($f$20) follows a similar mechanism as that in the muscle compartment, but in the liver, the influx depends only on the concentration of glucose in the blood rather than the glucose gradient, and there also exists a flux of glucose out of the tissue.

De Novo Lipogenesis (DNL)

The liver is the primary site for DNL in the body. The expression for DNL ($f$23) in liver is the same as that in the muscle compartment only here it depends on the concentration of glucose in the liver.

Glycogenesis/Glycogenolysis

Glycogen-glucose dynamics in the liver compartment are represented the same way as in the muscle compartment. During rigorous physical activity, liver glycogen is preferentially used as a source of glucose. To reproduce this specific behavior, an additional mechanism has been added in the model to enhance the glycogenolysis during physical activity ($f$21).

Gluconeogenesis from Amino Acids and Glycerol

The liver compartment is the site of gluconeogenesis. The model incorporates gluconeogenesis from glycerol ($f$24) as well from ketoacids ($f$30) and they are differentially regulated. Gluconeogenesis from ketoacids is assumed to be proportional to the concentration of ketoacids in the liver. However, gluconeogenesis from glycerol is inhibited by increased insulin sensitivity (IS) (input from the insulin resistance module).

Fatty Acid Metabolism

Unlike in the muscle, in the liver, there is no uptake of FFA from TGs and chylomicrons. There is uptake of FFAs from blood into liver that follows a 1st order process. The new FFA that is synthesized through DNL ($f23$) and FFA absorbed from blood are combined with glycerol to form TG ($f27$) that is transported out.

Ketogenesis

The model also incorporates a simplified representation of the ketogenesis ($f26$) that increases significantly when there is excess FFA in the liver compartment. Some of the ketone bodies are reconverted to FFA ($f25$) while the remaining is transported to blood over a gradient.

Detailed descriptions of the functions in the liver submodule are provided below.

TABLE 3.0

| Reaction | Equation |
| --- | --- |
| h(X) | $\dfrac{d}{1 + ae^{-c*(X-b)}}$ |
| $f_{19}$ | $\dfrac{C_{ADP,t}}{C_{ATP,total} - C_{ADP,t}}$ |
| $f_{20}$ | $((k_{glu_{b},liver,glut1} * C_{GLUT1} + k_{glu_{b},liver,glut4} * h(GLUT4)) * C_{glu,b})/(V_{liver})$ |
| $f_{21}$ | $k_{gly,glu_{liver}} * C_{gly,t} * \dfrac{1 + \alpha_{glycogenolysis,liver_{PA}} * (e^{\alpha_{epi,PA} * f_{PA}} - 1)}{1 + \left(\dfrac{r_{ATP,ADP}}{kI_{dg,atp}}\right)^{n_{dg,atp}}}$ |
| $f_{22}$ | $k_{glu,gly_{liver}} * (C_{gly,liver}^{max} - C_{gly,t}) * C_{glu,t} * IS$ |
| $f_{23}$ | $k_{glu,ffa_{liver}} * \dfrac{C_{glu,t}^{n_{glu,ffa}}}{C_{glu,t}^{n_{glu,ffa}} + km_{glu,ffa}^{n_{glu,ffa}}}$ |
| $f_{24}$ | $k_{glc,glu} * \dfrac{C_{glc,t}}{1 + \dfrac{IS}{kI_{gngf,insulin}}}$ |
| $f_{25}$ | $k_{kb,ffa} * C_{kb,t}$ |
| $f_{26}$ | $k_{ffa,kb} * \dfrac{C_{ffa,t}^{n_{ffa,kb}}}{C_{ffa,t}^{n_{ffa,kb}} + km_{ffa,kb}^{n_{ffa,kb}}}$ |
| $f_{27}$ | $k_{ffa,tg_{liver}} * C_{ffa,t} * C_{glc,t}$ |
| $f_{28}$ | $k_{p,aa_{liver}} * C_{p,t}$ |

TABLE 3.0-continued

| Reaction | Equation |
| --- | --- |
| $f_{29}$ | $k_{aa,p_{liver}} * C_{aa,t}$ |
| $f_{30}$ | $k_{ketoa,glu_{liver}} * C_{ketoa,t}$ |

2.3 Metabolism Module—Adipose Tissue Submodule

Figure 9:
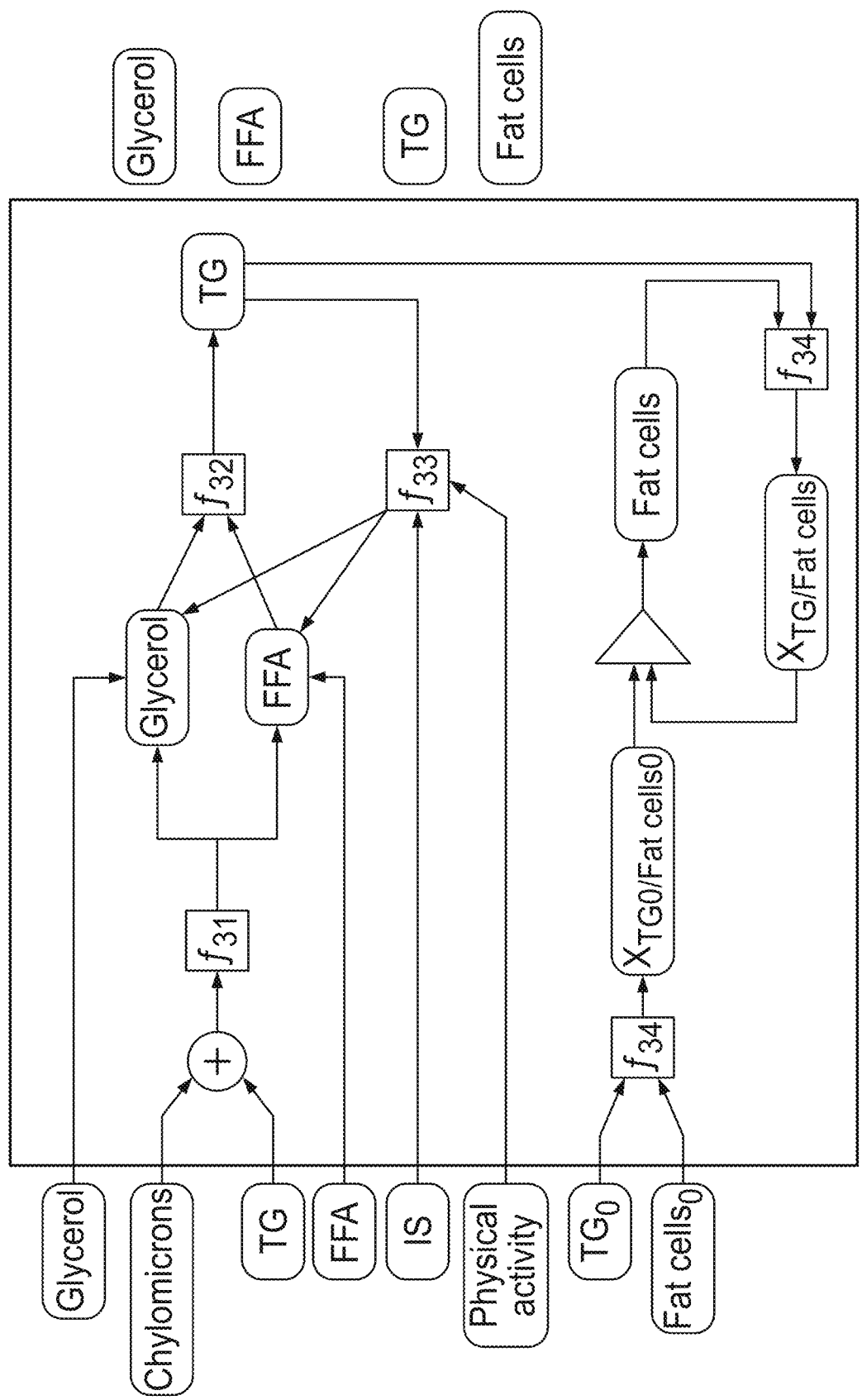
FIG. 9 is an exemplary diagram illustrating one embodiment of the adipose tissue subcomponent of the metabolism module of FIG. 5.

The adipose compartment represents the site of both visceral and subcutaneous fat tissue. The adipose compartment incorporates uptake of fat from blood, and the dynamic equilibrium between lipolysis and esterification. The fatty acid metabolism shown in FIG. 9 is the same as described in the muscle compartment, only adipose tissue absorbs more FFA from circulating TG and chylomicrons than muscle. Briefly, chylomicrons and triglycerides in blood are hydrolyzed to form FFA and glycerol which is absorbed into adipose tissue ($f31$). Glycerol is also synthesized in the adipose tissue. Some of the glycerol and FFA are re-esterified to form triglycerides which are stored in the adipose tissue ($f32$). The remaining is released back into blood.

During vigorous physical activity there is significantly increased lipolysis that is predominantly localized to the adipose tissue. Hence in the model, lipolysis in the adipose tissue is increased by exercise. The model also incorporates the regulation of lipolysis by insulin—increased insulin sensitivity decreases the rate of lipolysis ($f33$). When the fat content per fat cell—defined as triglyceride per fat cell increases above the baseline value, it drives the synthesis of new fat cells ($f34$).

Inputs into the adipose compartment model include:

Triglycerides
Free Fatty Acids (FFA)
Glycerol
Chylomicrons
IS

The adipose compartment integrates and calculates the following variables:

Free Fatty Acids (FFA)
Glycerol
Triglycerides
Adipocyte count

Detailed descriptions of the functions in the liver submodule are provided below.

TABLE 4.0

| Reaction | Equation |
| --- | --- |
| $f_{31}$ | $(k_{chy_{lpa,adipose}} * C_{chy,b} + (k_{tg_{lpa,adipose}} * C_{tg,b})/V_{adipose}$ |
| $f_{32}$ | $(k_{FFA_{tg,adipose}} * C_{ffa,t} * C_{glc,t})/V_{adipose}$ |
| $f_{33}$ | $\dfrac{k_{tgffa,adipose} * C_{tg,t} * k_{lipolysis,PA}}{1 + \left(\dfrac{IS}{kI_{lipolysis,insulin}}\right)^{n_{lipolysis,insulin}}}$ |
| $f_{34}$ | $C_{tg,t}/N_{ap}$ |
| $k_{lipolysis,PA}$ | $1 + \alpha_{lipolysis_{PA}} \left(\dfrac{\text{percent\_v02max}^{n_{lipolysis_{PA,adipose}}}}{\text{percent\_v02max}^{n_{lipolysis_{PA,adipose}}} + K_{m,lipolysis_{PA,adipose}}^{n_{lipolysis_{PA,adipose}}}}\right)$ |

3.0 Insulin Resistance Module

Figure 10A:
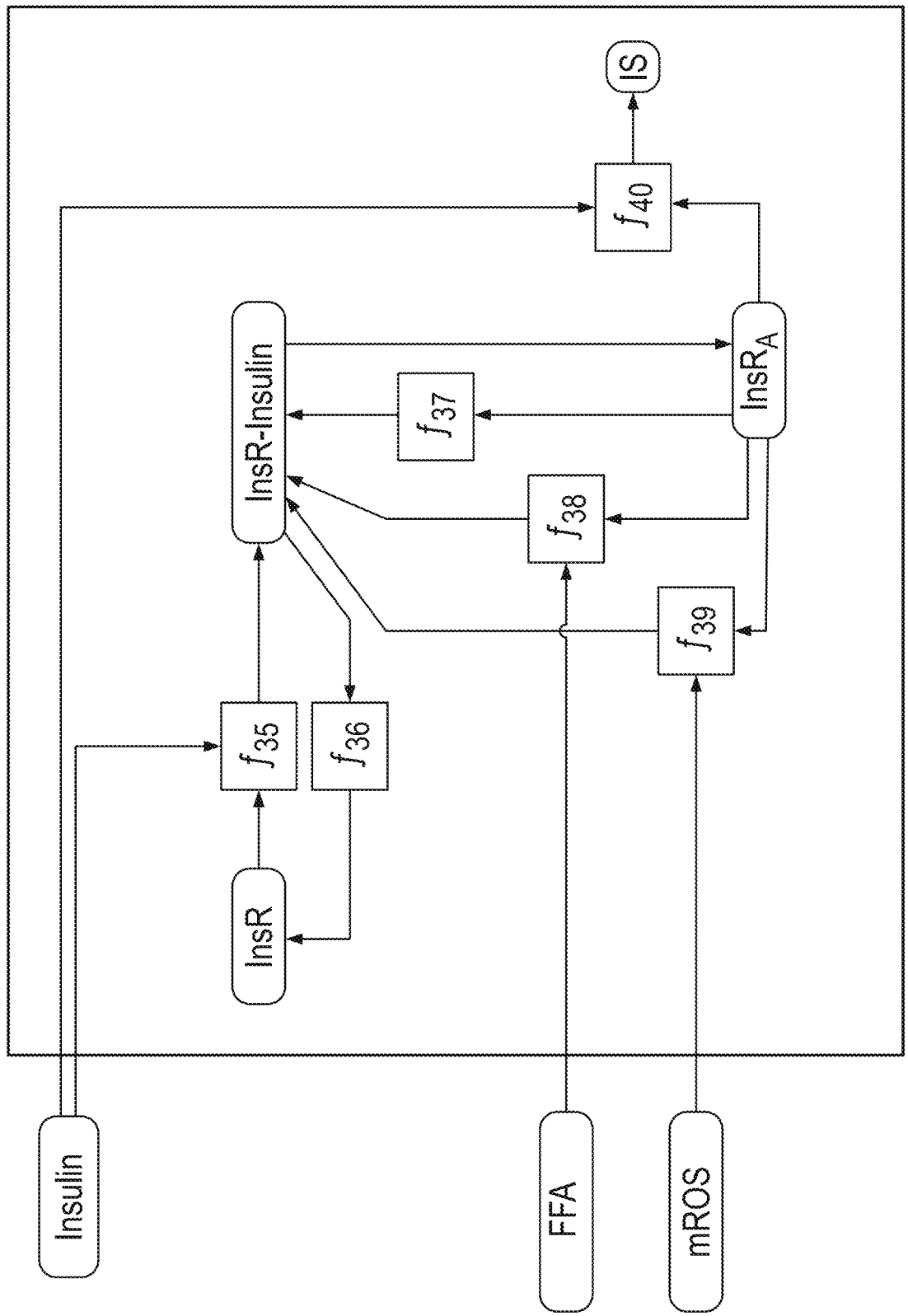
FIGS. 10A-B are exemplary data flow diagrams of another portion of one embodiment of the insulin module of FIG. 5.
Figure 10B:
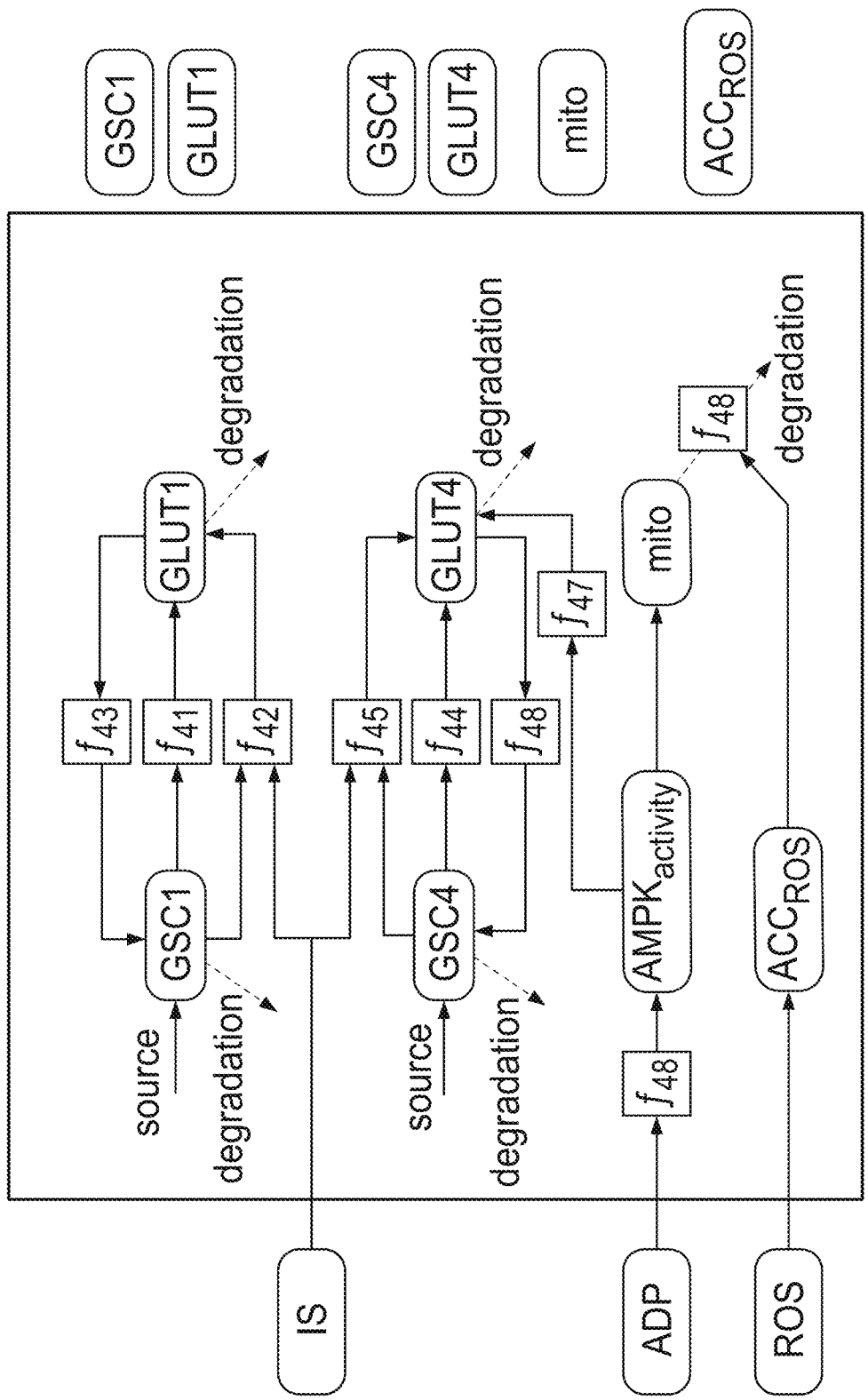

In the specific embodiments illustrated in FIGS. 10A and 10B, the insulin resistance (IR) module represents processes that modulate the following: a) the response of cells to insulin, b) short and long-term regulation of mitochondrial function, and c) the effects of energy depletion on AMPK activity.

Insulin (input from the insulin production module) binds ($f35$, $f36$) to the transmembrane insulin receptors (InsR) through a reversible reaction. The bound complex (InsR-Insulin) undergoes conformational changes to form the active form of the complex (InsRA). Reactive oxygen species (mROS) (input from the muscle compartment and described in Table 2) and serum FFA (input from the blood component) have been shown to increase the natural rate of dephosphorylation of the insulin-insulin receptor complex ($f37$, $f38$, $f39$). Since the dynamics of insulin receptor phosphorylation and dephosphorylation is significantly faster than the dynamics of insulin, FFA etc., a quasi-steady state approximation was used to convert the differential equations for the two forms of the receptors into algebraic equations. Insulin sensitivity is expressed as the fraction of insulin receptors which are in the phosphorylated (active) state (InsRA), further normalized by the level of InsRA at steady-state and expressed as IS ($f40$).

The concentrations of glucose transporters (GLUT1 and GLUT4) on the cell surface regulate the permeability of glucose transport into cells as illustrated in FIG. 10B. The model represents the dynamics of GLUT1 and GLUT4 concentrations on the cell surface as well as the intracellular concentrations. Both transporters undergo endocytosis through a first order process. Both GLUT1 and GLUT4 transport to the cell surface by regular transport ($f41$, $f44$) but also controlled ($f42$, $f45$) by changing insulin sensitivity (IS). However, GLUT4 transport is highly responsive to increases in insulin concentrations but not GLUT1. GLUT4 transport to the cell surface is further increased by AMPK activity ($f47$). Inside the cell, GLUT1 transporters (GSC1) is synthesized at a constant rate and degraded using a first order process. Intracellular GLUT4 (GSC4) is controlled by the same mechanism. Both GLUT1 and GLUT4 undergo endocytosis ($f43$, $f46$) to bring it back inside the cell.

Mitochondrial function (half-life of 3 days) controls macronutrient oxidation, thereby controlling the rate of generation of ATP. ATP deficiency (or ADP excess) leads to upregulation of AMPK activity that in turn increases the synthesis of mitochondria. In the model, concentration of adenosine monophosphate (AMP) is assumed to be proportional to that of ADP. ADP concentration controls the AMPK activity through a Hill function ($f48$). Mitochondrial synthesis in the model is directly proportional to AMPK activity. Age-dependent cumulative ROS leads to increased rate of degradation of mitochondria. The instantaneous mROS level is a function of macronutrient oxidation (input from the muscle component) which is integrated into the cumulative term for ROS. The accumulated ROS drives the degradation of mitochondria ($f49$).

Inputs into the insulin resistance compartment model include:

Serum insulin
Free Fatty Acids (FFA)
mROS from muscle compartment
ADP from muscle compartment The insulin resistance compartment integrates and calculates an estimate, over time, of the following parameters:

Insulin sensitivity (IS)
GSC1
GSC4
Mitochondrial function
accumulated ROS
GLUT4
GLUT1

Detailed descriptions of the functions in the liver sub-module are provided below.

TABLE 5.0

| | |
|---|---|
| $f_{35}$ | $k_{on}C_{insulin,b}C_{insR} - k_{off}C_{insR-insulin}$ |
| $f_{36}$ | $k_{recycle}C_{insR-insulin}$ |
| $f_{37}$ | $k_{auto}C_{insRA}$ |
| $f_{38}$ | $k_{ri_{inact},ffa}C_{insRA}\dfrac{C^n_{ffa,muscle}}{C^n_{ffa,muscle}+EC50^n_{ffa,muscle}}$ |
| $f_{39}$ | $k_{ri_{inact},ROS}C_{insRA}C_{ROS}$ |
| $v_1$ | $\left(\dfrac{(k_{off}+k_{ract})}{(Kd_{insulinR}*(f_{37}+f_{38}+f_{39}))} - \dfrac{k_{on}}{(f_{37_{ss}}+f_{38_{ss}}+f_{39_{ss}})}\right)C_{insulin,b}$ |
| $v_2$ | $C_{insulin,b}/Kd_{insulinR}$ |
| $f_{40}$ | $\dfrac{v_1*C^{total}_{insR}}{(1+v_1+v_2)} \bigg/ \dfrac{v_{1_{ss}}*C^{total}_{insR}}{\left(1+v_{1_{ss}}+v_{2_{ss}}\right)}$ |
| $f_{41}$ | $k_{recycle,GSC1}C_{GSC1}$ |
| $f_{42}$ | $k_{recycle,GSC1,insulin}C_{GSC1}C_{insRA}$ |
| $f_{43}$ | $k_{internalization,GLUT1}C_{GLUT1}$ |
| $f_{44}$ | $k_{recycle,GSC4}C_{GSC4}$ |
| $f_{45}$ | $k_{recycle,GSC4,insulin}C_{GSC4}C_{insRA}$ |
| $f_{46}$ | $k_{internalization,GLUT4}C_{GLUT4}$ |
| $f_{47}$ | $k_{recycle,GSC1,insulin}C_{GSC1}C_{AMPK}$ |
| $f_{48}$ | $k_{AMPK,ADP}\dfrac{C^{n_{AMPK,ADP}}_{ADP}}{C^{n_{AMPK,ADP}}_{ADP}+Km^{n_{AMPK,ADP}}_{AMPK,ADP}}$ |
| $f_{49}$ | $d_{mito,ROS}C_{mito}C_{AUCROS}$ |

4.0 Insulin Production Module (Pancreas)

In various embodiments, the insulin production module can comprise a model of the pancreas described in De Gaetano et al. "*Mathematical models of diabetes progression,*" Am. J. Physiol. Endocrinol. Metab., 295:E1462, 2008, which includes the production of insulin by the pancreas as a function of plasma glucose levels and active pancreatic beta cells. This paper is hereby incorporated herein by reference in its entirety for all purposes.

For example, insulin is produced by pancreatic beta cells as a function of blood glucose and fat levels and active beta cells. The number of active beta cells increases with increasing levels of blood glucose. Chronic inflammation and oxidative stress due reactive oxygen species (ROS), generated as a result of over-nutrition or other factors, damages beta cells and accelerates apoptosis. Some beta cells spontaneously recover from this damage, but conditions such as chronic hyperglycemia lead to steadily decreasing pancreatic capacity and hence reduced insulin production. This reduction in insulin production is one of the driving factors in development of diabetes.

Accordingly, in various embodiments, the insulin production module can be configured to estimate an individual's current pancreatic reserve of beta cells and predict amount of insulin produced in the pancreas. In various embodiments the model can account for growth of beta cells and damage done to them by reactive molecules.

The insulin production module may be coupled with other modules in various suitable ways. For example, the glucose and free fatty acids data (i.e., present in the blood) may be provided by the blood module as an input to the insulin production module. The insulin production module also may provide insulin data to the blood module, and such insulin data can be communicated to the insulin sensitivity module where glucose uptake can be regulated. The insulin production module also may provide insulin data to the blood module 231, and such insulin data then may be communicated to the metabolism module where such insulin data may influence estimations of gluconeogenesis, proteolysis, lipolysis, esterification, glycogenesis, and the like.

Figure 11:
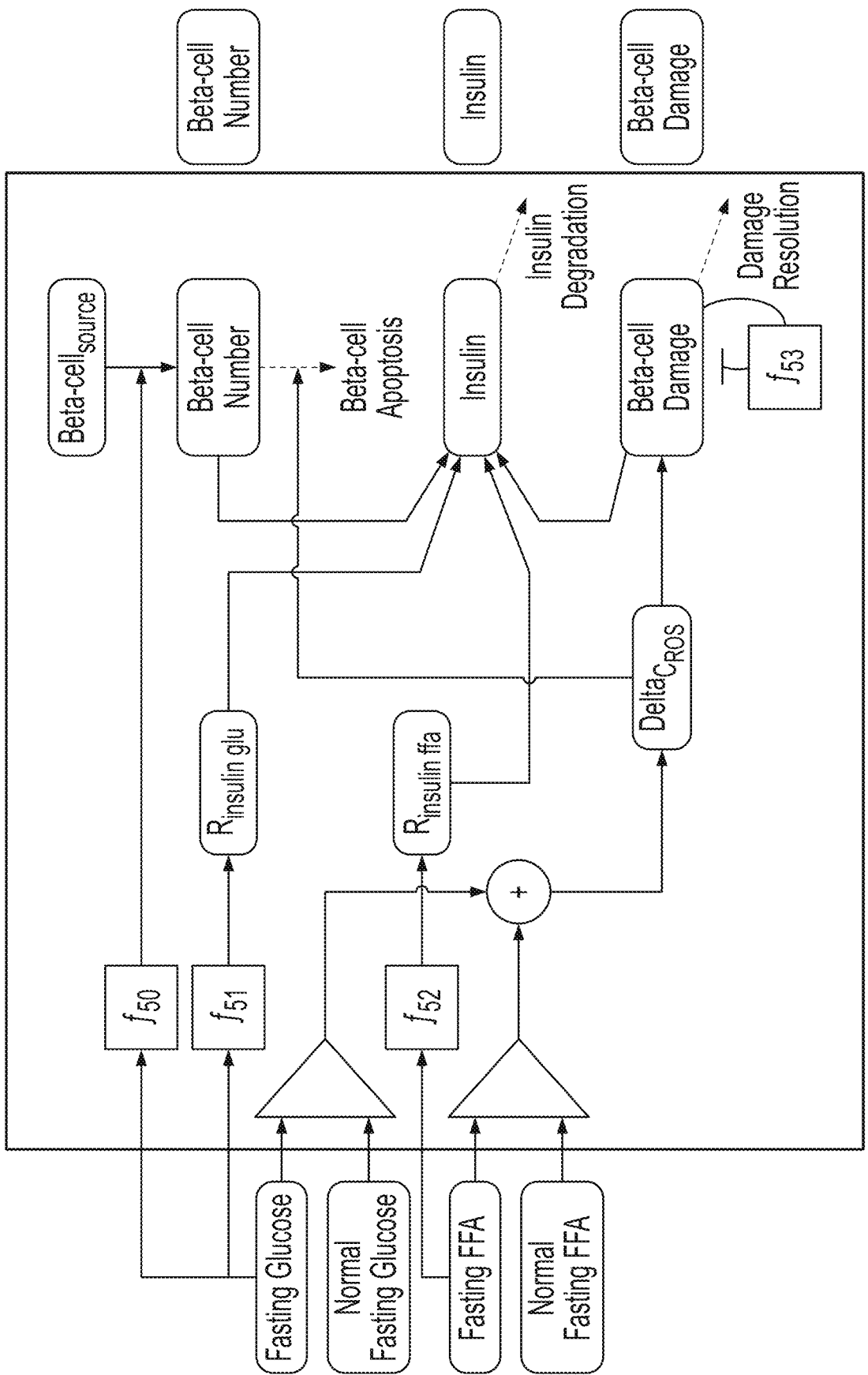
FIG. 11 is an exemplary data flow diagram of another portion of one embodiment of the insulin module of FIG. 5.

The presently-described pancreas model is a modification of that of De Gaetano et al. (2008). The model incorporates the long-term dynamics of beta cell mass, beta cell function and insulin production as shown in FIG. 11. Proliferation of beta cells is represented as a Hill function dependent on blood glucose (input from blood component) concentration (ƒ50). Beta cell apoptosis is a function of chronic inflammation in the form of ROS. ROS in this module is represented as being generated by combination of serum glucose and serum FFA in excess of their normal levels respectively ($\Delta C_{ROS}$). Beta cell function bounded between 0 and 1 is decreased at a rate proportional to remaining beta cell function and ROS concentrations (ƒ52). The beta cell function recovers following a 1st order process.

The rate of insulin production is proportional to the beta cell number, beta cell functional capacity (1−beta cell damage) and product of a Hill function (ƒ51) of serum glucose concentration ($R_{insulin,glu}$) and a separate Hill function (ƒ52) of serum FFA concentration ($R_{insulin, ffa}$). Insulin is removed from blood following a 1st order process.

Inputs into the insulin production compartment model include serum glucose and serum FFA. The insulin production compartment integrates and calculates an estimate, over time, of pancreatic beta cell count, beta cell damage, and serum insulin concentration.

Detailed descriptions of the functions in the liver submodule are provided below.

TABLE 6.0

| | |
|---|---|
| $f_{50}$ | $k_{betacells,glu} \dfrac{C_{glu,b}^{n_{betacells,glu}}}{C_{glu,b}^{n_{betacells,glu}} + Km_{betacells,glu}^{n_{betacells,glu}}}$ |
| $f_{51}$ | $k_{insulin,glu} \dfrac{C_{glu,b}^{n_{betacells,glu}}}{C_{glu,b}^{n_{betacells,glu}} + Km_{betacells,glu}^{n_{insulin,glu}}}$ |
| $f_{52}$ | $\dfrac{(1)}{\left(1 + \left(\dfrac{C_{ffa,b}}{kI_{insulin,ffa}}\right)^{n_{insulin,ffa}}\right)}$ |
| $\Delta C_{ROS}$ | $k_{ros,glu}(C_{glu,b} - C_{glu,bss}) + k_{ros,ffa} \dfrac{(C_{ffa,b} - C_{ffa,bss})}{(C_{ffa,b} - C_{ffa,bss}) + Km_{ros,glu}}$ |
| $f_{53}$ | $k_{bc_{damage},ROS} \Delta C_{ROS}(1 - C_{bc_{damage}})$ |

Calculation of Weight:

Weight of the whole body is calculated based on concentrations of glycogen, protein and fat. The water associated with these macronutrients is also taken into account.

TABLE 7.0

| | |
|---|---|
| Glycogen | $C_{glycogen,liver}V_{liver} + C_{glycogen,muscle}V_{muscle}$ |
| Protein | $C_{protein,liver}V_{liver} + C_{protein,muscle}V_{muscle}$ |
| Fat | $C_{TG,liver}V_{liver} + C_{TG,muscle}V_{muscle} + C_{TG,adipose}V_{adipose}$ |
| FFM | (hydration$_{fat}$Fat + 0.25 * Weight$_{ss}$ + Protein + Glycogne)/hydration$_{ffm}$ |
| Weight | FFM + Fat |

Use Case 1: Population Study

The goal of this study was to predict the effect of lifestyle-interventions on pre-diabetic patients based on their time course of weight and HbA1c measurements and the onset of diabetes.

We were granted access to the publicly released DPP data through the National Institute of Diabetes and Digestive and Kidney Diseases (NIDDK). We examined data collected from study participants through baseline, quarterly, mid-year, and annual medical visits over three years of the DPP study in order to have a sufficient number of patients for time-course analysis. The variables extracted, including patient identifiers, demographic information, and clinical measurements.

The computational model of diabetes was used to calibrate to the time course data of placebo subjects in the DPP study. The age, height and gender of each patient were provided as input, while time course of weight (Kg) (W), HbA1c (%), fasting serum glucose (mM) and fasting serum insulin (pM) were used to calibrate the model. From initial review it was observed that if the diet reported in the study was directly used as an input to the model, it made it extremely difficult for the model to match the time course of measurements for the above-mentioned variables during the study. Previous studies have shown that diet reporting is often unreliable, so we accounted for incorrect diet reporting by using correction factors for the diet both before and during the study. There were 12 parameters that were varied on an individual patient basis to match the experimental data.

The parameters were estimated by using weighted least squares estimation using the differential evolution algorithm. The form of the objective function was:

$$\Phi(\theta) = \sum_i \sum_j w_{ij}(y_{ij} - y_{ij}^*)^2$$

i=[W,$C_{HbA1c}^B$,$C_G^B$,$C_I^B$] and j=1,n$_i$ where n$_i$ is the number of data point available for the i$^{th}$ variable during the study. w$_{ij}$ represents the weight for the i$^{th}$ variable at the j$^{th}$ time point.

Baseline Calibration Data

In various embodiments, the baseline calibration of the model serves as an initial starting point for further calibration to specific individuals and populations. For example, to calculate the baseline calibration of the model to the general US population, various publicly available data sets are used. One such data set is the National Health and Nutrition Examination Survey (NHANES) data set. NHANES is a nationally commissioned health survey sponsored by the Center for Disease Control and Prevention (CDC) to record and publish individual health conditions over time. A model can be calibrated to a specific demographic within the NHANES dataset using a Synthetic Panel Data (SPD) method, or the like. SPD can be used to approximate longitudinal data from non-longitudinal data sets. The SPD method works by identifying an age cohort of interest and then shifts the age of that cohort to take the progression of time.

Figure 14:
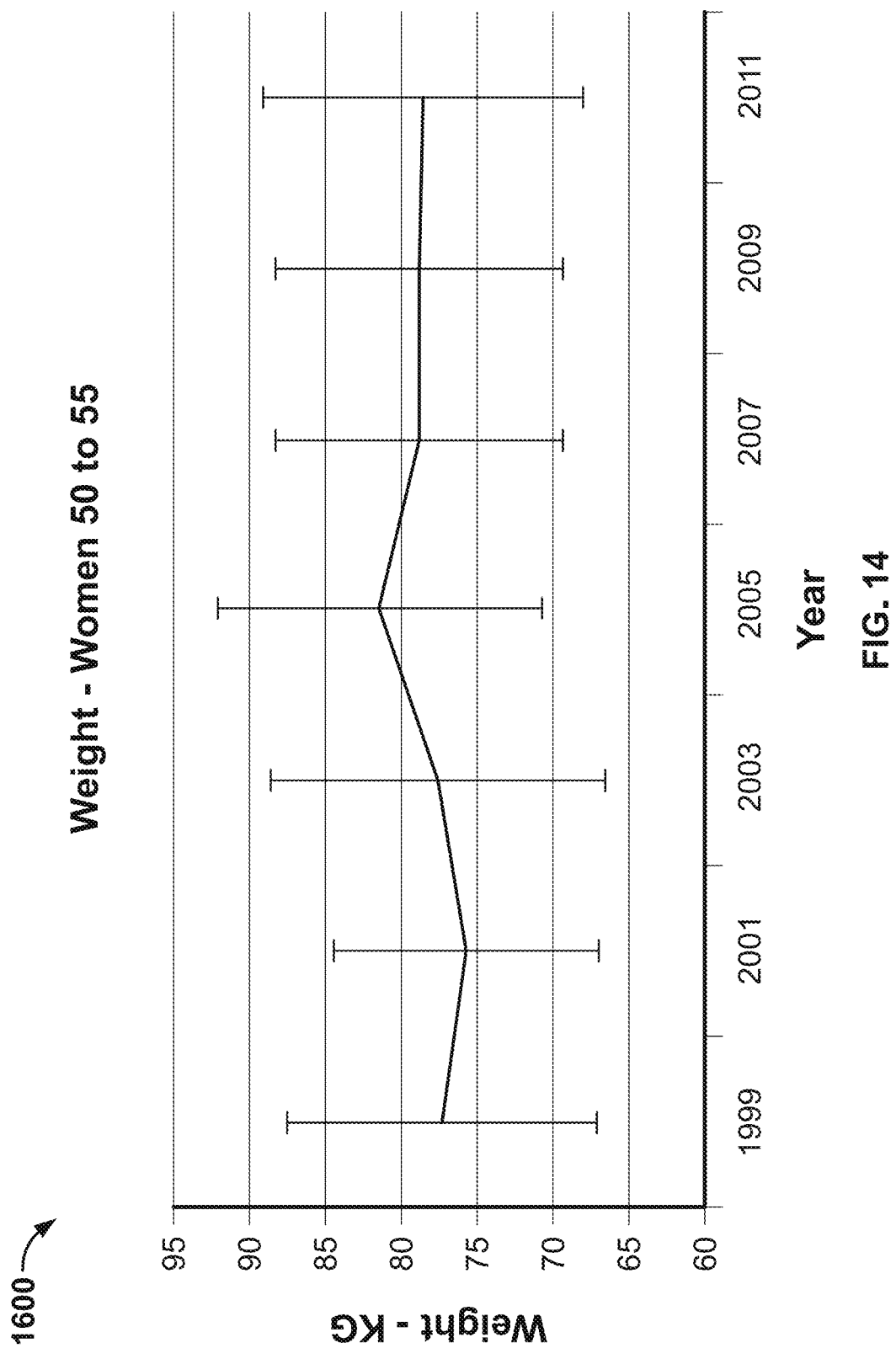
FIG. 14 is a graph of a set of calibration data over time based on the data illustrated in FIGS. 12 and 13.

For example FIGS. 12A-D and 13A-C show bar graphs of the body weight for women initially between the ages of 50-55 starting in 1999 and then in 2001, 2003, 2005, 2007, 2009 and 2011 respectively. The NHANES data set is tracked through time using the SPD method. Once the time progression of demographic measurement has been extracted using SPD, a time series of that measurement can be generated for use in calibrating the model. For example, FIG. 14 illustrates a set of calibration data 1600 over time.

In several embodiments, other data available from sources like published scientific literature, electronic health records, prescription data, claims data, and the like could also be used similarly for baseline calibration.

Calibration of Diabetes Model to Patients from the Lifestyle Intervention Arm

The computational model of diabetes was calibrated to the time course of a small set of patients from the Lifestyle intervention arm of the DPP study. The same patient characteristics (e.g., age, gender etc.) and time course (e.g., weight, HbA1c etc.) were used for the calibration.

To accurately model and simulate health outcomes to match known data at individual or population levels, various calibration methodologies can be used to train the model to data of interest. In some embodiments, the calibration process utilizes an Approximate Bayesian Computation method to non-parametrically estimate the posterior parameters distribution. In some embodiments, a large number of parameters may need to be estimated, so a Markov Chain Monte Carlo can be used to find parameter values to simulate observed population level statistics.

In some embodiments, the calibration process utilizes evolutionary optimization algorithm. Evolutionary algorithms are a class of stochastic, global optimization algorithms that can follow heuristics based on the process of biological evolution of a population. For example, the calibration process could use differential evolution, a type of evolutionary algorithm that searches for the optimum solution using a population of candidate solutions.

In various embodiments other known local or global optimization algorithms could be used either in isolation or in combination, as suitable for the calibration problem.

In various embodiments, a given model can use a combination of user specified initial conditions and/or inputs over time to predict model outputs. The calibration process can generate a set of acceptable parameters to match the model's simulated outputs to the observed data from the individual or population of interest. For example, Table 1 below illustrates the four example types of values in the calibration process of one embodiment.

| Type of Value | Description | Example |
| --- | --- | --- |
| Initial Conditions | Data about condition of individual/ population at simulation start time | 1. Demographic data about gender, ethnicity and current height and age<br>2. Behavioral information including, for example, physical activity (e.g., calories burned during exercise or other activity), alcohol consumption, and diet (e.g., kcals obtained from fat, carbs and proteins, and the like)<br>3. Serum HbA1c concentration<br>4. Current Insulin Resistance |
| Parameters | Factors internal to the model, varies by individual/ population | Resting metabolic rate<br>Excess caloric intake<br>EC50(FFA)<br>Beta-cell apoptosis rate |
| Inputs | Time varying information used by model to calculate outputs. | 1. Diet (e.g, kcals obtained from fat, carbs and proteins, and the like)<br>2. Physical activity (e.g., calories burned during exercise or other activity) |
| Outputs | Model forecasted variable that evolve over time | 1. Predicted Weight<br>2. Predicted Insulin Resistance<br>3. Predicted metabolic and/or physiological parameters (e.g., serum HbA1c concentration, serum glucose, serum insulin) |

Using the same strategy as the calibration of placebo patients, the under-reporting of the diets by the Lifestyle intervention arm subjects was taken into account by adding additional parameters to estimate the amount of underreporting during the pre-study and study periods. To prevent the addition of too many free parameters, the change in physical activity that is significant for this arm is directly determined by the documented physical activity, assuming it was reported accurately.

The reported physical activity for the subjects was often found to be varying during the study period. For the purposes of this study, we assumed a linear trend in activity over time and used a Python package to fit a linear regression model to the activity data in order to define an intercept and slope that represents the activity of each Lifestyle cohort patient during the 3 year study. The best fit patients, as defined by, $R^2 > 0.85$ were selected for subsequent selection and calibration. Similar to the placebo population, statistical tests were used to compare the model output to the real data from the study.

Model Validation

The goal of the study is to be able to predict the effect of lifestyle-interventions on pre-diabetic patients based on their time course of weight and HbA1c measurements and the onset of diabetes. The DPP study lifestyle-intervention arm was not designed with a specific intervention that all patients were expected to follow. As a result, every patient in the study had a unique lifestyle-intervention. Individual patient parameter estimation providing the model with the patient demographics and only the baseline measurement would lead to too many combinations of parameters without any ability to choose between them which makes it unsuitable for prediction of response to lifestyle-intervention. Hence, for the purposes of model validation the following strategy was used:

Each placebo patient was assigned a unique lifestyle-intervention based on the lifestyle-interventions observed in the real patients and simulated.

The distribution of the simulated model output for weight and HbA1c would be compared to the distribution of real measurements from the patients of the lifestyle-intervention arm of the study.

The rate of onset of diabetes from the simulated patients would be compared to the rate of onset of diabetes in the real patients in the lifestyle-intervention arm of the study.

It was observed that the baseline distribution of age, weight and HbA1c of the placebo patients when compared to those of the patients in the lifestyle-intervention arm did not pass 2-sample KS test with 95% confidence level. This necessitated that a sub-sample of patients from the placebo patients be chosen whose baseline measurements would be statistically similar to those of the lifestyle-intervention subjects.

The two attributes to the change in physical activity (namely intercept and slope) during the study were analyzed and found to be independent of all patient attributes. However, intercept and slope parameters themselves show a loose correlation (correlation coefficient=−0.43). These two parameters were thus generated randomly from the original distributions (preserving the correlation coefficient) and assigned to each placebo patient.

Each placebo patient was then compared to the 60 patients from the lifestyle-intervention arm used in calibration using nearest neighbor analysis. The patient attributes used in the computation of nearest neighbor were—patient age and 6 patient parameters namely (metabolic need for carbohydrate and fat, consumption of carbohydrate and fat before the study and consumption during the study). The parameters were normalized using Z-score method and Euclidian distance metric was used as described below.

$$\delta_i = (\theta_i - \bar{\theta}_i)/\sigma_i$$

$$d = \sqrt{\Sigma(\delta_i - \delta_i^*)^2}$$

$\theta_i$ represents the $i^{th}$ patient attribute, $\bar{\theta}_i$ and $\sigma_i$ represent the mean and standard deviation of the attribute across the population of patients; $\delta i$ represents the normalized attribute; $\delta i^*$ represents the normalized parameter value of the test placebo patient; d represents the Euclidian distance of the test patient compared to a single patient from the population of patients used in calibration of lifestyle-intervention patients. The nearest neighbor defined by the patient with the minimum value of d was identified and the change in intake of carbohydrate and fat as estimated from model calibration was assigned to the placebo patient. Each placebo patient was therefore assigned all 4 parameters related to lifestyle change—change in physical activity (intercept and slope) and change in intake of carbohydrate and fat. These placebo patients with unique lifestyle-interventions were simulated and model output compared to the real patients of the lifestyle-intervention arm as described above.

Analysis of Results

Role of Parameters in Diabetes Progression

The goal of this analysis was to identify if there are statistically significant differences between the estimates of specific parameters between the subjects who went on to develop diabetes in the 3 years from the start of the study in comparison to those subjects who did not. To maximize the difference between the parameters, the change in HbA1c during the years of the study was collected and the patients whose changes in HbA1c were between minimum and 1st quartile (group 1) and those between 3rd quartile and maximum (group 2) were separated into two different populations. For these 2 populations, 2-sample KS test was performed to compare the parameter distributions for each parameter independently. In addition, using a binary classification group 1 being 0 and group 2 being 1, the populations were processed using a classification decision tree using scikit-learn python package and the resultant decision-tree is analyzed.

Discussion of Results

We use the computational model of diabetes to calibrate to the time courses of 4 clinical variables for all subjects from the placebo arm as described above. The model is able to accurately fit to all 4 variables simultaneously in greater than 80% of cases. Comparison of model output to the experimental individual subject data is done both at an individual subject level as well as an aggregate population level.

Four examples subjects are shown (FIGS. 15A, B, C, D), which demonstrate the model's ability to match the experimental data. These four subjects were chosen because they show very different time course. The data points show the time course of real measurements for the patients and the line represents the model simulation for the same period of time based on the calibrated parameters. The subjects in FIG. 15A shows an increase in weight and simultaneous increase in HbA1c. However, subject in FIG. 15B shows a decrease in weight with no real improvement in the HbA1c. FIG. 15D represents a subject that had both a reduction in weight and HbA1c levels. The model accurately predicted the dynamics in all cases.

At the aggregate population level, the histograms of experimental data for weight and HbA1c are generated for both experimental data and simulated model output for baseline and every year thereafter. The simulated model output closely matches the distribution of the experimental data at year 3 as seen in FIGS. 16A-D.

As described above, a small subset of subjects from the lifestyle-intervention arm were used for model calibration. The predictions for the effect of lifestyle interventions were generated by simulating the selection group of placebo subjects with individual lifestyle interventions as described above. Comparison of the distributions of weight and HbA1c at year 3 between the experimental data and predicted model output are shown.

To further provide evidence, statistical comparison of the two distributions is done at year 3 and shown below.

|  | Baseline | Placebo Year 3 | Lifestyle intervention Year 3 |
| --- | --- | --- | --- |
| Weight | 0.76 | 0.99 | 0.15 |
| HbA1c | 0.64 | 0.85 | 0.06 |

There is no statistically significant difference between the distributions based on study data and model predictions (p-value >0.05).

Use Case 2: Individual Study

To train and test the model against individual level human data, we used data from a weight loss study by Gardner et al., in which they randomized 61 overweight adults to low-fat (LF) or low-carbohydrate (LC) diets for a 6-month period (Obesity (Silver Spring). 2016 January; 24(1):79-86. doi: 10.1002/oby.21331. Epub 2015 Dec. 6). Data for each subject were recorded at baseline, 3 months and 6 months and included self-reported diet captured via a 24-hr dietary recall, and measured body weight, blood glucose and fasting insulin among others. At the end of the 6 months, a diet crossover was performed so that the LF subjects switched to LC and vice versa and continued for another 6 months. Data were collected at 9 and 12 months. Of the 61 participants, 41 were selected for further analysis in this study, as they had no missing data for diet, body weight, blood glucose, and insulin measurements. To provide additional training data to the model, we estimated fat mass and fat free mass from the measured body weight time course.

We selected subset of the base parameters of the model using our understanding of the model structure and calibrated these parameters separately for each individual to train the model to individual data recorded in the weight loss study. After training the selected parameters separately to each individual, the dynamics of change in body weight, fat mass, fat free mass, fasting blood glucose and fasting insulin were captured quantitatively by the model within acceptable error. A typical example of the model fitted to an individual is shown in FIGS. 17A and B. In order to quantify how well the "model" fit to each individual, we calculated an aggregated error of fit for the individuals. The aggregated error showed that the model could capture dynamics of 37 out of the 41 (~90%) individuals within acceptable limits.

Results—Prediction of Weight Loss

Figure 17:
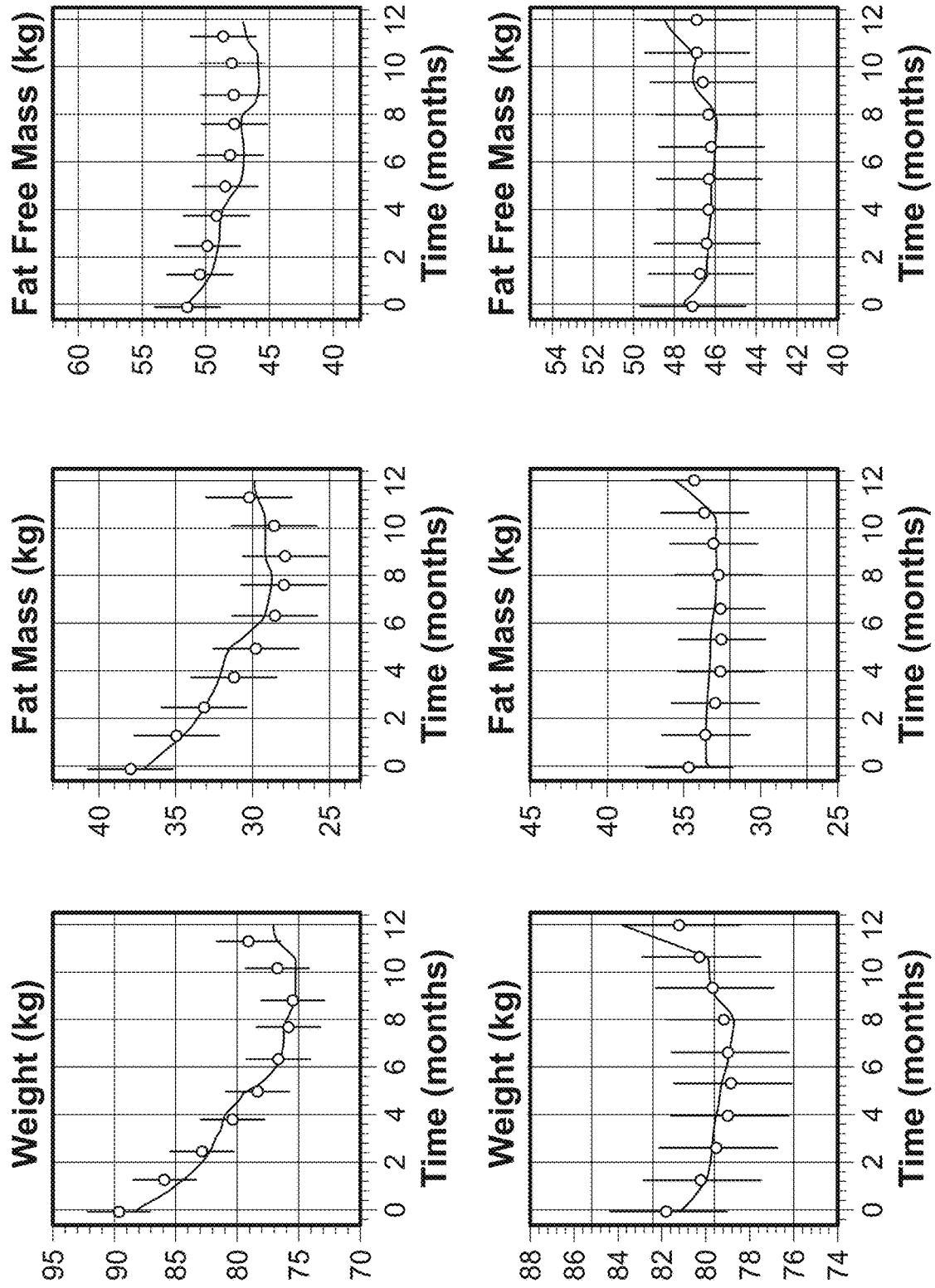
FIG. 17 illustrates one example of fitting to a first data set and predicting a second data set (data for weight, fat mass and fat free mass) for 2 example individuals.

In order to validate the model, a cross-validation strategy was used in which the data set for each subject of the weight loss study was split into two complementary parts. Data set 1 corresponded to first 6 months of the study on one type of diet (either LC or LF). Data set 2 comprised of data from the latter 6 months of the study, when the subjects had switched their diets. The model was trained using an approach similar to that described above, but we only used data set 1 in the training process. After determining the parameters for each individual by training to data set 1, the last 6 months of the study was simulated and compared the predictions with data set 2. The large majority of the predictions fell within acceptable measurement error of the variables and the model captured general trends of the measured values very well. A typical example of fitting to data set 1 and predicting data set 2 is illustrated in FIGS. 17 (A-B) (dotted vertical line represents the 6-month mark demarcating the switch from dataset 1 to dataset 2). In order to assess the quality of prediction for the entire group of subjects, an aggregated fitness score identical to the one described above was used. The number of individuals that fit well was not as high as it was when the entire data set was used for training; however, the model successfully predicted time dependent changes in the variables of more than 70% individuals as seen in FIG. 17 (in each figure right of the dotted line represents prediction).

Figure 18:
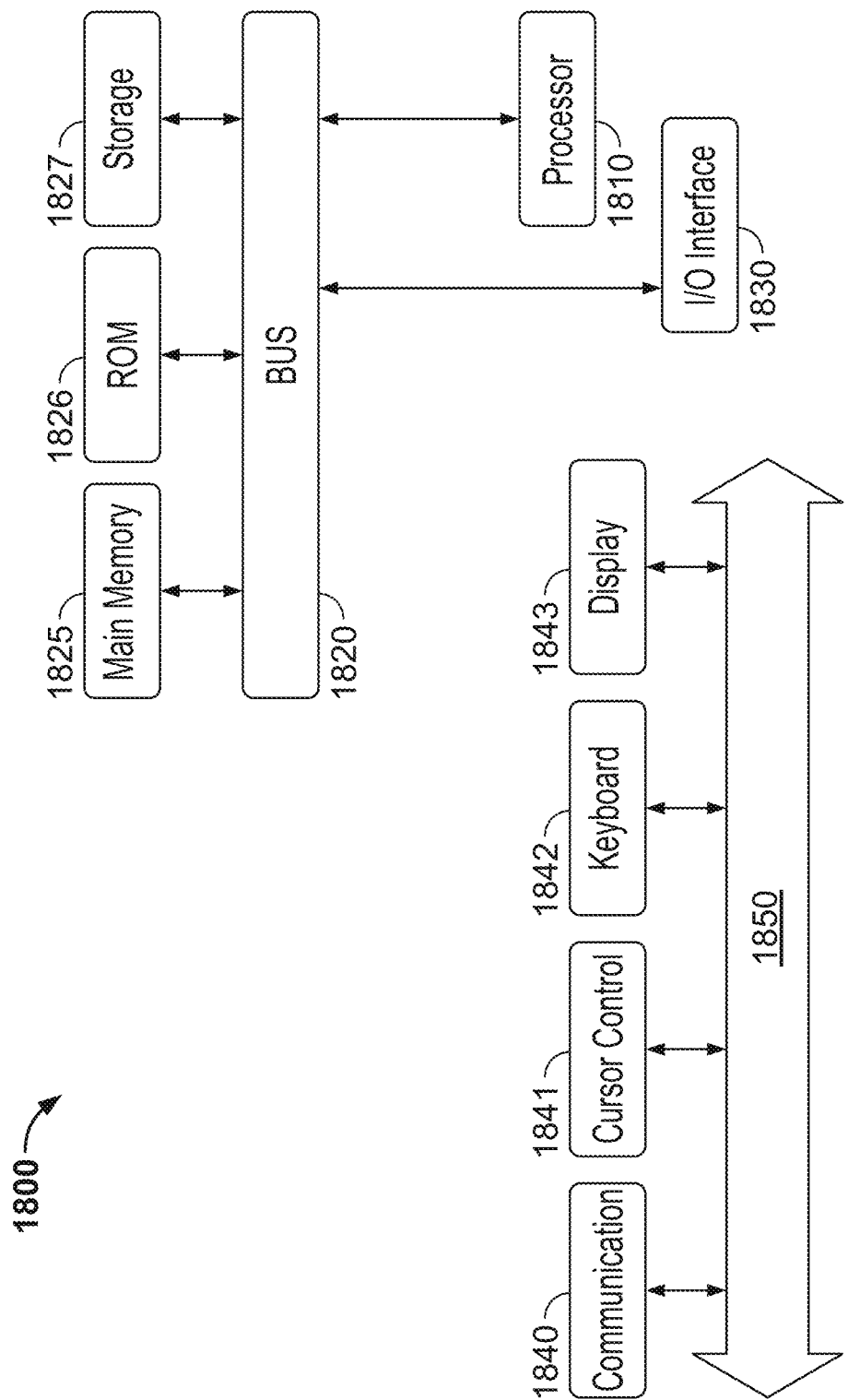
FIG. 18 illustrates one embodiment of an exemplary computer architecture for use with the present method of simulating a biological process of FIG. 1.

As previously mentioned, FIG. 18 illustrates an exemplary computer architecture 1800 for use with the health and body simulation systems disclosed herein, according to one embodiment. One embodiment of architecture 1800 comprises a system bus 1820 for communicating information, and a processor 1810 coupled to bus 1820 for processing information. Architecture 1800 further comprises a random access memory (RAM) or other dynamic storage device 1825 (referred to herein as main memory), coupled to bus 1820 for storing information and instructions to be executed by processor 1810. Main memory 1825 also may be used for storing temporary variables or other intermediate information during execution of instructions by processor 1810. Architecture 1800 also may include a read only memory (ROM) and/or other static storage device 1826 coupled to bus 1820 for storing static information and instructions used by processor 1810.

A data storage device 1827 such as a magnetic disk or optical disc and its corresponding drive may also be coupled to computer system 1800 for storing information and instructions. Architecture 1800 can also be coupled to a second I/O bus 1850 via an I/O interface 1830. A plurality of I/O devices may be coupled to I/O bus 1850, including a display device 1843, an input device (e.g., an alphanumeric input device 1842 and/or a cursor control device 1841).

The communication device 1840 allows for access to other computers (servers or clients) via a network. The communication device 1840 may comprise one or more modems, network interface cards, wireless network interfaces or other well-known interface devices, such as those used for coupling to Ethernet, token ring, or other types of networks.

In the description above, for purposes of explanation only, specific nomenclature is set forth to provide a thorough understanding of the present disclosure. However, it will be apparent to one skilled in the art that these specific details are not required to practice the teachings of the present disclosure.

Some portions of the detailed descriptions herein are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the below discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present disclosure also relates to an apparatus for performing the operations herein. This apparatus may be specially constructed for the required purposes, or it may comprise a general purpose computer selectively activated or reconfigured by a computer program stored in the computer. Such a computer program may be stored in a non-transitory computer readable storage medium, such as, but is not limited to, any type of disk, including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms presented herein are not inherently related to any particular computer or other apparatus. Various general purpose systems, computer servers, or personal computers may be used with programs in accordance with the teachings herein, or it may prove convenient to construct a more specialized apparatus to perform the required method steps. The required structure for a variety of these systems will appear from the description herein. It will be appreciated that a variety of programming languages may be used to implement the teachings of the disclosure as described herein.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter. It is also expressly noted that the dimensions and the shapes of the components shown in the figures are designed to help to understand how the present teachings are practiced, but not intended to limit the dimensions and the shapes shown in the examples.

The described embodiments are susceptible to various modifications and alternative forms, and specific examples thereof have been shown by way of example in the drawings and are herein described in detail. It should be understood, however, that the described embodiments are not to be limited to the particular forms or methods disclosed, but to the contrary, the present disclosure is to cover all modifications, equivalents, and alternatives.

What is claimed is:

1. A method for predicting a time to diabetes onset in a subject, comprising:
   a. determining, for the subject, subject parameter values comprising height, weight, age, gender, fasting blood glucose concentration, and serum HbA1c concentration at a first time;
   b. calculating initial parameter set values comprising basal metabolic rate, excess caloric intake, EC50(FFA), and beta cell apoptosis rate based on the subject parameter values by
      (i) setting an age estimate to an age younger than the age determined in step (a), setting a weight estimate to a weight that is different from the weight determined in step (a), setting a fasting blood glucose concentration estimate to a value different from the fasting blood glucose concentration determined in step (a), and setting a serum HbA1c estimate to a value different from the serum HbA1c concentration determined in step (a),
      (ii) providing an initial estimate for each value in the initial parameter set values at the age estimate,
      (iii) iteratively calculating the initial parameter set values, the weight estimate, the fasting blood glucose concentration estimate, and the serum HbA1c estimate, in a time-dependent manner in which the age estimate is increased by a first time step in each iteration from the age estimate set in step (b)(i) until the age estimate is substantially equal to the age, and
      (iv) iteratively performing steps (ii)-(iii) until the weight estimate is substantially equal to the weight, the fasting blood glucose concentration estimate is substantially equal to the fasting blood glucose concentration, and the serum HbA1c estimate is substantially equal to the serum HbA1c concentration when the age estimate is substantially equal to the age;
   c. iteratively calculating a future time and a projected fasting blood glucose concentration using the initial parameter set calculated in step (b)(iii) and the subject parameter values, in a time-dependent manner in which the first time is increased by a second time step in each iteration until the projected fasting blood glucose concentration at the future time is calculated to be greater than 125 mg/dL;
   d. identifying the future time iteratively calculated in step (c) as the time to diabetes onset; and
   e. displaying the future time identified in step (d) as the predicted time for diabetes onset.

2. The method of claim 1, wherein the age estimate set in step (b)(i) is at least one year less than the age.

3. The method of claim 1, wherein the weight estimate set in step (b)(i) is less than the weight.

4. The method of claim 1, wherein the serum HbA1c estimate set in step (b)(i) is less than 3%.

5. The method of claim 1, wherein the fasting blood glucose concentration estimate set in step (b)(i) is less than 100 mg/dL.

6. The method of claim 1, wherein the first time step is 5-365 days.

7. The method of claim 6, wherein the first time step is constant for all iterations.

8. The method of claim 1, wherein the second time step is 5-365 days.

9. The method of claim 8, wherein the second time step is constant for all iterations.

10. The method of claim 1, wherein receiving the subject parameter values comprises:
    receiving raw health data from one or more of patient specific electronic medical records, published clinical studies, claims data, prescription data, patient biomarkers, and wearable user devices;
    receiving health data about the subject; and
    determining the subject parameter values of the subject based on the received raw health data and the received subject health data.

11. The method of claim 1, wherein performing step (iv) comprises:
    adding a perturbation factor to one or more of the initial estimates for the initial parameter set values, wherein the perturbation factor is configured to be adjustable in each increase to increase an accuracy of calculating the initial parameter set values.

12. The method of claim 1, wherein performing step (c) of iteratively calculating the future time and the projected fasting blood glucose concentration comprises:
    receiving time-varying information comprising diet information, physical activity information, or both diet information and physical activity information; and
    applying the time-varying information during each of the iteratively calculated future time and projected fasting blood glucose concentration.

13. The method of claim 12, wherein the time-varying information comprises the diet information, and wherein the diet information comprises consumption rates or amounts for a plurality of macronutrients.

14. The method of claim 13, wherein the plurality of macronutrients comprises carbohydrates, fats, and proteins.

15. A system, comprising a processor and a non-transitory memory computer readable medium storing programming instructions executable by the processor, wherein the programming instructions comprise:
    a. determining, for the subject, subject parameter values comprising height, weight, age, gender, fasting blood glucose concentration, and serum HbA1c concentration at a first time;
    b. calculating initial parameter set values comprising basal metabolic rate, excess caloric intake, EC50(FFA), and beta cell apoptosis rate based on the subject parameter values by
       (i) setting an age estimate to an age younger than the age determined in step (a), setting a weight estimate to a weight that is different from the weight determined in step (a), setting a fasting blood glucose concentration estimate to a value different from the fasting blood glucose concentration determined in step (a), and setting a serum HbA1c estimate to a value different from the serum HbA1c concentration determined in step (a), (ii) providing an initial estimate for each value in the initial parameter set values at the age estimate, (iii) iteratively calculating the initial parameter set values, the weight estimate, the fasting blood glucose concentration estimate, and the serum HbA1c estimate, in a time-dependent manner in which the age estimate is increased by a first time step in each iteration from the age estimate set in step (b)(i) until the age estimate is substantially equal to the age, and (iv) iteratively performing steps (ii)-(iii) until the weight estimate is substantially equal to the weight, the fasting blood glucose concentration estimate is substantially equal to the fasting blood glucose concentration, and the serum HbA1c estimate is substantially equal to the serum HbA1c concentration when the age estimate is substantially equal to the age;

c. iteratively calculating a future time and a projected fasting blood glucose concentration using the initial parameter set calculated in step (b)(iii) and the subject parameter values, in a time-dependent manner in which the first time is increased by a second time step in each iteration until the projected fasting blood glucose concentration at the future time is calculated to be greater than 125 mg/dL;

d. identifying the future time iteratively calculated in step (c) as the time to diabetes onset; and e. displaying the future time identified in step (d) as the predicted time for diabetes onset.

16. The system of claim 15, wherein the age estimate set in step (b)(i) is at least one year less than the age.

17. The system of claim 15, wherein the weight estimate set in step (b)(i) is less than the weight.

18. The system of claim 15, wherein the serum HbA1c estimate set in step (b)(i) is less than 3%.

19. The system of claim 15, wherein the fasting blood glucose concentration estimate set in step (b)(i) is less than 100 mg/dL.

20. The system of claim 15, wherein the first time step is 5-365 days.

21. The system of claim 20, wherein the first time step is constant for all iterations.

22. The system of claim 15, wherein the second time step is 5-365 days.

23. The system of claim 22, wherein the second time step is constant for all iterations.

24. The system of claim 15, wherein receiving the subject parameter values comprises:
  receiving raw health data from one or more of patient specific electronic medical records, published clinical studies, claims data, prescription data, patient biomarkers, and wearable user devices;
  receiving health data about the subject; and
  determining the subject parameter values of the subject based on the received raw health data and the received subject health data.

25. The system of claim 15, wherein performing step (iv) comprises:
  adding a perturbation factor to one or more of the initial estimates for the initial parameter set values, wherein the perturbation factor is configured to be adjustable in each increase to increase an accuracy of calculating the initial parameter set values.

26. The system of claim 15, wherein performing step (c) of iteratively calculating the future time and the projected fasting blood glucose concentration comprises:
  receiving time-varying information comprising diet information, physical activity information, or both diet information and physical activity information; and
  applying the time-varying information during each of the iteratively calculated future time and projected fasting blood glucose concentration.

27. The system of claim 26, wherein the time-varying information comprises the diet information, and wherein the diet information comprises consumption rates or amounts for a plurality of macronutrients.

28. The system of claim 27, wherein the plurality of macronutrients comprises carbohydrates, fats, and proteins.

* * * * *